(12) United States Patent
Davidson et al.

(10) Patent No.: US 9,169,483 B2
(45) Date of Patent: Oct. 27, 2015

(54) RNA INTERFERENCE SUPPRESSION OF NEURODEGENERATIVE DISEASES AND METHODS OF USE THEREOF

(71) Applicant: University of Iowa Research Foundation, Iowa City, IA (US)

(72) Inventors: Beverly L. Davidson, Iowa City, IA (US); Alejandro Mas Monteys, Iowa City, IA (US); Ryan L. Boudreau, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 13/933,146

(22) Filed: Jul. 2, 2013

(65) Prior Publication Data
US 2014/0163214 A1 Jun. 12, 2014

Related U.S. Application Data

(63) Continuation of application No. 12/977,812, filed on Dec. 23, 2010, now Pat. No. 8,487,088, which is a continuation of application No. 12/111,025, filed on Apr. 28, 2008, now abandoned.

(60) Provisional application No. 60/914,309, filed on Apr. 26, 2007.

(51) Int. Cl.
*C12N 15/00* (2006.01)
*C07H 21/02* (2006.01)
*C12N 5/00* (2006.01)
*C12N 15/113* (2010.01)

(52) U.S. Cl.
CPC ........ *C12N 15/113* (2013.01); *C12N 2310/111* (2013.01); *C12N 2310/14* (2013.01); *C12N 2310/141* (2013.01); *C12N 2310/53* (2013.01)

(58) Field of Classification Search
None
See application file for complete search history.

(56) References Cited

U.S. PATENT DOCUMENTS

| | | | |
|---|---|---|---|
| 5,139,941 A | 8/1992 | Muzyczka et al. | |
| 5,173,414 A | 12/1992 | Lebkowski et al. | |
| 5,720,720 A | 2/1998 | Laske et al. | |
| 7,902,352 B2 | 3/2011 | Kaemmerer et al. | |
| 2002/0114780 A1 | 8/2002 | Bankiewicz et al. | |
| 2002/0141980 A1 | 10/2002 | Bankiewicz et al. | |
| 2002/0187127 A1 | 12/2002 | Bankiewicz | |
| 2004/0162255 A1 | 8/2004 | Kaemmerer | |
| 2005/0096284 A1 | 5/2005 | McSwiggen | |
| 2005/0255086 A1 | 11/2005 | Davidson et al. | |
| 2006/0257912 A1 | 11/2006 | Kaemmerer et al. | |
| 2010/0008981 A1 | 1/2010 | Kaemmerer et al. | |
| 2010/0325746 A9 | 12/2010 | Kaemmerer et al. | |

FOREIGN PATENT DOCUMENTS

| | | |
|---|---|---|
| WO | WO 2004/047872 A2 | 6/2004 |
| WO | WO 2005/105995 A2 | 11/2005 |
| WO | WO 2006/083800 A2 | 8/2006 |
| WO | WO 2007/022506 A2 | 2/2007 |
| WO | WO 2007/089584 A2 | 8/2007 |

OTHER PUBLICATIONS

Cai et al., "Human microRNAs are processed from capped, polyadenylated transcripts that can alos function as mRNAs", *RNA* 10, 1957-1966 (2004).

Patent Cooperation Treaty International Search Report and Written Opinion of the International Searching Authority for PCT/US2008/061791, 17 pages, Feb. 25, 2009.

Lee et al., "MicroRNA genes are transcribed by RNA polymerase II", *EMBO Journal*, 23, 4051-4060 (2004).

Liu et al., "Specific inhibition of Huntington's disease gene expression by siRNAs in cultured cells", *Proc.Japan Acad.*, 79, Ser. B, No. 10, pp. 293-298, 2003.

McBride et al., "Artificial miRNAs mitigate shRNA-mediated toxicity in the brain: Implications for the therapeutic development of RNAi", *PNAS*, vol. 105, No. 15, pp. 5868-5873, 2008.

Rodriguez-Lebron, et al., "Intrastriatal rAAV-Mediated Delivery of Anti-huntingtin shRNAs Induces Partial Reversal of Disease Progression in R6/1 Huntington's Disease Transgenic Mice", *Molecular Therapy* vol. 12, No. 4, pp. 618-633, 2005.

Wang et al., "Clinico-pathological rescue of a model mouse of Huntington's disease by siRNA", *Neuroscience Research* 53, pp. 241-249, 2005.

*Primary Examiner* — Richard Schnizer
(74) *Attorney, Agent, or Firm* — Viksnins Harris & Padys PLLP

(57) ABSTRACT

The present invention is directed to RNA interference (RNAi) molecules targeted against a nucleic acid sequence that encodes poly-glutamine repeat diseases, and methods of using these RNAi molecules.

17 Claims, 6 Drawing Sheets

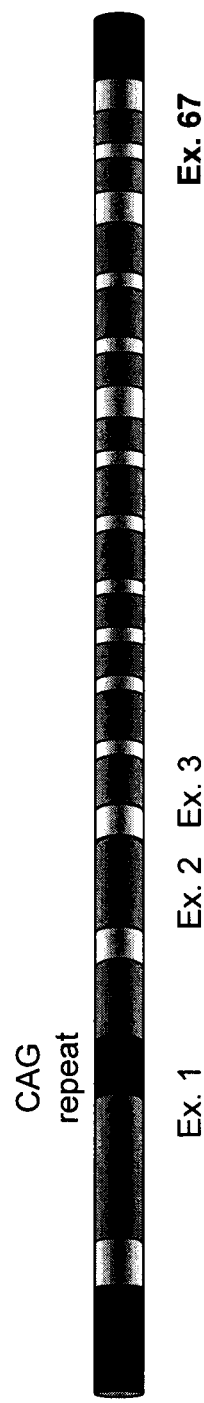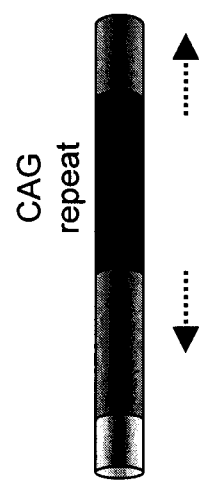
Figure 1A
Figure 1B

Figure 2
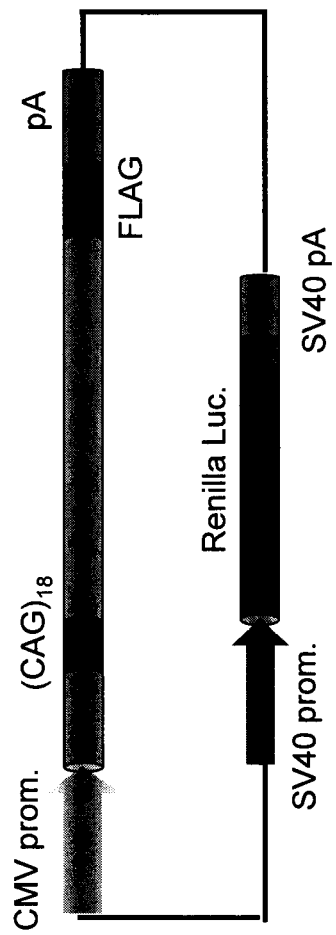
Fig. 2A
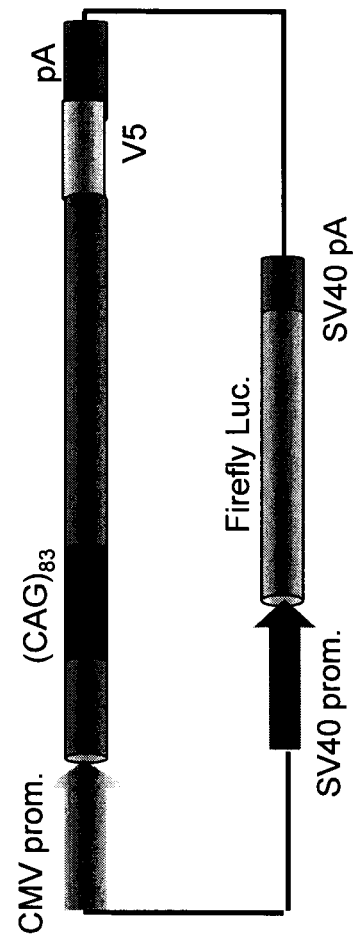
Fig. 2B

SEQUENCE LISTING

```
<160> NUMBER OF SEQ ID NOS: 16

<210> SEQ ID NO 1
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
augaaggccu ucgagucccu c                                              21

<210> SEQ ID NO 2
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
ggcgacccug gaaaagcuga u                                              21

<210> SEQ ID NO 3
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
uggcgacccu ggaaaagcug a                                              21

<210> SEQ ID NO 4
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
auggcgaccc uggaaaagcu g                                              21

<210> SEQ ID NO 5
<211> LENGTH: 94
<212> TYPE: RNA
<213> ORGANISM: Artificial Sequence
<220> FEATURE:
<223> OTHER INFORMATION: Description of Artificial Sequence: Synthetic
      polynucleotide
```

```
<400> SEQUENCE: 5
aaaacucgag ugagcgcuga aggccuucga gucccucacc guaaagccac agauggguga    60
gggacucgaa ggccuucauc gccuacuagu aaaa                                94

<210> SEQ ID NO 6
<211> LENGTH: 94
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 6
aaaacucgag ugagcgcuga aggccuucga gucuuuuacc guaaagccac agauggguga    60
gggacucgaa ggccuucauc gccuacuagu aaaa                                94

<210> SEQ ID NO 7
<211> LENGTH: 94
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 7
aaaacucgag ugagcgcaug aaggccuucg agucccuccc guaaagccac agauggggag    60
ggacucgaag gccuucaucc gccuacuagu aaaa                                94

<210> SEQ ID NO 8
<211> LENGTH: 94
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 8
aaaacucgag ugagcgcaug aaggccuucg agucuuuucc guaaagccac agauggggag    60
ggacucgaag gccuucaucc gccuacuagu aaaa                                94

<210> SEQ ID NO 9
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
acacaggaag gggaauauca cacucugggg au                                  32

<210> SEQ ID NO 10
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
acacaggaag gggau                                                     15

<210> SEQ ID NO 11
```

-continued

<210> SEQ ID NO 11
<211> LENGTH: 31
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
acacaggaag gggaauauca cacucuggga u                                      31

<210> SEQ ID NO 12
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
cacaggaagg ggaauaucac acucugggga                                        30

<210> SEQ ID NO 13
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
cacaggaagg ggaauaucac acucuggga                                         29

<210> SEQ ID NO 14
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
cacaggaagg gga                                                          13

<210> SEQ ID NO 15
<211> LENGTH: 54
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
cagcagcagc agcagcagca gcagcagcag cagcagcagc agcagcagca gcag             54

<210> SEQ ID NO 16
<211> LENGTH: 249
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 16

```
cagcagcagc agcagcagca gcagcagcag cagcagcagc agcagcagca gcagcagcag        60
cagcagcagc agcagcagca gcagcagcag cagcagcagc agcagcagca gcagcagcag       120
cagcagcagc agcagcagca gcagcagcag cagcagcagc agcagcagca gcagcagcag       180
cagcagcagc agcagcagca gcagcagcag cagcagcagc agcagcagca gcagcagcag       240
cagcagcag                                                               249
```

RNA INTERFERENCE SUPPRESSION OF NEURODEGENERATIVE DISEASES AND METHODS OF USE THEREOF

PRIORITY OF INVENTION

This application is a continuation application of U.S. application Ser. No. 12/977,812, which was filed on Dec. 23, 2010, which is a continuation application of U.S. application Ser. No. 12/111,025, which was filed on Apr. 28, 2008, which application is related to and claims priority under 35 U.S.C. §119(e) to U.S. Provisional Application No. 60/914,309 filed on Apr. 26, 2007, which are incorporated by reference herein.

BACKGROUND OF THE INVENTION

Double-stranded RNA (dsRNA) can induce sequence-specific posttranscriptional gene silencing in many organisms by a process known as RNA interference (RNAi). However, in mammalian cells, dsRNA that is 30 base pairs or longer can induce sequence-nonspecific responses that trigger a shutdown of protein synthesis. RNA fragments are the sequence-specific mediators of RNAi. Interference of gene expression by these RNA interference (RNAi) molecules is now recognized as a naturally occurring strategy for silencing genes in the cells of many organisms.

SUMMARY OF THE INVENTION

The dominant polyglutamine expansion diseases, which include Huntington's disease (HD), are progressive, untreatable neurodegenerative disorders. In inducible mouse models of HD, repression of mutant allele expression improves disease phenotypes. Thus, therapies designed to inhibit disease gene expression would be beneficial. The present invention provides methods of using RNAi in vivo to treat dominant neurodegenerative diseases. "Treating" as used herein refers to ameliorating at least one symptom of, curing and/or preventing the development of a disease or a condition.

In certain embodiment of the invention, RNAi molecules are employed to inhibit expression of a target gene. By "inhibit expression" is meant to reduce, diminish or suppress expression of a target gene. Expression of a target gene may be inhibited via "gene silencing." Gene silencing refers to the suppression of gene expression, e.g., transgene, heterologous gene and/or endogenous gene expression, which may be mediated through processes that affect transcription and/or through processes that affect post-transcriptional mechanisms. In some embodiments, gene silencing occurs when an RNAi molecule initiates the degradation of the mRNA transcribed from a gene of interest in a sequence-specific manner via RNA interference, thereby preventing translation of the gene's product.

The present invention provides an isolated RNA duplex (under physiological conditions) comprising a first strand of RNA and a second strand of RNA, wherein the first strand comprises at least 15 contiguous nucleotides encoded by HDAS 07 (SEQ ID NO:1), HDAS 18 (SEQ ID NO:2), HDAS 19 (SEQ ID NO:3) or HDAS 20 (SEQ ID NO:4), and wherein the second strand is complementary to at least 12 contiguous nucleotides of the first strand. As used herein the term "encoded by" is used in a broad sense, similar to the term "comprising" in patent terminology. For example, the statement "the first strand of RNA is encoded by SEQ ID NO:1" means that the first strand of RNA sequence corresponds to the RNA sequence transcribed from the DNA sequence indicated in SEQ ID NO:1, but may also contain additional nucleotides at either the 3' end or at the 5' end of the RNA molecule.

The reference to siRNAs herein is meant to include shRNAs and other small RNAs that can or are capable of modulating the expression of HD gene, for example via RNA interference. Such small RNAs include without limitation, shRNAs and miroRNAs (miRNAs).

In certain embodiments, the RNA duplex described above is between 15 and 30 base pairs in length, such as between 19 and 25 base pairs, such as 19 or 21 base pairs in length. In certain embodiments, the first and/or second strand further comprises an overhang, such as a 3' overhang region, a 5' overhang region, or both 3' and 5' overhang regions. The two strands of RNA in the siRNA may be completely complementary, or one or the other of the strands may have an "overhang region" (i.e., a portion of the RNA that does not bind with the second strand). Such an overhang region may be from 1 to 10 nucleotides in length.

In certain embodiments, in the RNA duplex described above, the first strand and the second strand are operably linked by means of an RNA loop strand to form a hairpin structure to form a duplex structure and a loop structure. In certain embodiments, the loop structure contains from 4 to 50 nucleotides. In certain embodiments, the loop structure contains from 4 to 10 nucleotides, such as 4, 5 or 6 nucleotides.

In certain embodiments, the loop portion is designed to circumvent exportin-5 mediated export. The loop can vary in length. In some embodiments the loop is 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length. In certain embodiments, the loop portion is a 30 nucleotide L1 motif. In certain embodiments, the loop portion is about 12 to 50 nucleotides long, or is about 20 to 40 nucleotides long, or is about 25 to 35 nucleotides long, or is about 30 nucleotides long. In certain embodiments, the loop portion is a 32 nucleotide L1 motif. In certain embodiments, the loop portion comprises between 12 and 32 nucleotides of SEQ ID NO:9. In certain embodiments, the loop portion comprises between 12 and 32 contiguous nucleotides of SEQ ID NO:9. In certain embodiments, the loop portion consists of SEQ ID NO:12, SEQ ID NO:13, or SEQ ID NO:14. Exemplary loop portions are provided below:

```
NES-long #1:
                                        (SEQ ID NO: 9)
5'-ACACAGGAAG GGGAAUAUCA CACUCUGGGG AU-3'

NES-long #2:
                                        (SEQ ID NO: 11)
5'-ACACAGGAAG GGGAAUAUCA CACUCUGGGA U-3'

NES-short:
                                        (SEQ ID NO: 10)
5'-ACACAGGAAG GGGAU-3'

NES-long #1:
                                        (SEQ ID NO: 12)
5'-CACAGGAAGG GGAAUAUCAC ACUCUGGGA-3'

NES-long #2:
                                        (SEQ ID NO: 13)
5'-CACAGGAAGG GGAAUAUCAC ACUCUGGGA-3'

NES-short:
                                        (SEQ ID NO: 14)
5'-CACAGGAAGG GGA-3'
```

The present invention further provides expression cassettes containing a nucleic acid encoding HDAS 07 (SEQ ID NO:1), HDAS 18 (SEQ ID NO:2), HDAS 19 (SEQ ID NO:3), HDAS 20 (SEQ ID NO:4), miHD7A-1 (SEQ ID NO:5), miHD7A-2

(SEQ ID NO:6), miHD7B-1 (SEQ ID NO:7), or miHD7B-2 (SEQ ID NO:8). The expression cassette may further contain a promoter, such as a regulatable promoter or a constitutive promoter. Examples of suitable promoters include a CMV, RSV, pol II or pol III promoter. The expression cassette may further contain a polyadenylation signal (such as a synthetic minimal polyadenylation signal) and/or a marker gene. Examples of marker genes include visual markers such as GFP, or functional markers, such as antibiotic resistance genes.

The present invention also provides vectors containing an expression cassettes containing a nucleic acid encoding HDAS 07 (SEQ ID NO:1), HDAS 18 (SEQ ID NO:2), HDAS 19 (SEQ ID NO:3), HDAS 20 (SEQ ID NO:4), miHD7A-1 (SEQ ID NO:5), miHD7A-2 (SEQ ID NO:6), miHD7B-1 (SEQ ID NO:7), or miHD7B-2 (SEQ ID NO:8). The present invention provides a vector containing a first expression cassette and a second expression cassette, wherein the first expression cassette contains a first nucleic acid encoding at least 15 contiguous nucleotides encoded by HDAS 07 (SEQ ID NO:1), HDAS 18 (SEQ ID NO:2), HDAS 19 (SEQ ID NO:3) or HDAS 20 (SEQ ID NO:4), and the second expression cassette contains a second nucleic acid encoding at least 12 contiguous nucleotides complementary to the first strand. Examples of appropriate vectors include adenoviral, lentiviral, adeno-associated viral (AAV), poliovirus, HSV, or murine Maloney-based viral vectors. In one embodiment, the vector is an adenoviral vector. In certain embodiments, a vector may contain two expression cassettes, a first expression cassette containing a nucleic acid encoding the first strand of the RNA duplex and a second expression cassette containing a nucleic acid encoding the second strand of the RNA duplex.

The present invention provides cells (such as a mammalian cell) containing an expression cassette expression containing a nucleic acid encoding HDAS 07 (SEQ ID NO:1), HDAS 18 (SEQ ID NO:2), HDAS 19 (SEQ ID NO:3), HDAS 20 (SEQ ID NO:4), miHD7A-1 (SEQ ID NO:5), miHD7A-2 (SEQ ID NO:6), miHD7B-1 (SEQ ID NO:7), or miHD7B-2 (SEQ ID NO:8); a vector containing an expression cassettes containing a nucleic acid encoding HDAS 07 (SEQ ID NO:1), HDAS 18 (SEQ ID NO:2), HDAS 19 (SEQ ID NO:3), HDAS 20 (SEQ ID NO:4), miHD7A-1 (SEQ ID NO:5), miHD7A-2 (SEQ ID NO:6), miHD7B-1 (SEQ ID NO:7), or miHD7B-2 (SEQ ID NO:8); or a vector containing a first expression cassette and a second expression cassette, wherein the first expression cassette contains a first nucleic acid encoding at least 15 contiguous nucleotides encoded by HDAS 07 (SEQ ID NO:1), HDAS 18 (SEQ ID NO:2), HDAS 19 (SEQ ID NO:3) or HDAS 20 (SEQ ID NO:4), and the second expression cassette contains a second nucleic acid encoding at least 12 contiguous nucleotides complementary to the first strand. The present invention also provides a non-human mammal containing these expression cassettes or vectors described herein. In certain embodiments, the vector is an adenoviral, lentiviral, adeno-associated viral (AAV), poliovirus, HSV, or murine Maloney-based viral vector.

The present invention provides a method of suppressing the accumulation of huntingtin in a cell by introducing a ribonucleic acid (RNA) duplex into the cell in an amount sufficient to suppress accumulation of huntingtin in the cell, wherein the RNA duplex contains (a) an isolated or purified miRNA consisting of miHD7A-1 (SEQ ID NO:5), miHD7A-2 (SEQ ID NO:6), miHD7B-1 (SEQ ID NO:7), or miHD7B-2 (SEQ ID NO:8); (b) a first strand of RNA and a second strand of RNA, wherein the first strand contains at least 15 contiguous nucleotides encoded by HDAS 07 (SEQ ID NO:1), HDAS 18 (SEQ ID NO:2), HDAS 19 (SEQ ID NO:3) or HDAS 20 (SEQ ID NO:4), and wherein the second strand is complementary to at least 12 contiguous nucleotides of the first strand; (c) a vector containing an expression cassettes containing a nucleic acid encoding HDAS 07 (SEQ ID NO:1), HDAS 18 (SEQ ID NO:2), HDAS 19 (SEQ ID NO:3), HDAS 20 (SEQ ID NO:4), miHD7A-1 (SEQ ID NO:5), miHD7A-2 (SEQ ID NO:6), miHD7B-1 (SEQ ID NO:7), or miHD7B-2 (SEQ ID NO:8); or (d) a vector containing a first expression cassette and a second expression cassette, wherein the first expression cassette contains a first nucleic acid encoding at least 15 contiguous nucleotides encoded by HDAS 07 (SEQ ID NO:1), HDAS 18 (SEQ ID NO:2), HDAS 19 (SEQ ID NO:3) or HDAS 20 (SEQ ID NO:4), and the second expression cassette contains a second nucleic acid encoding at least 12 contiguous nucleotides complementary to the first strand. In certain embodiments, the accumulation of huntingtin is suppressed by at least 10%. The accumulation of huntingtin is suppressed by at least 10%, 20%, 30%, 40%, 50%, 60%, 70%, 80%, 90% 95%, or 99%.

The present invention provides a method of preventing cytotoxic effects of mutant huntingtin in a cell by introducing a ribonucleic acid (RNA) duplex into the cell in an amount sufficient to suppress accumulation of huntingtin, and wherein the RNA prevents cytotoxic effects of huntingtin in the cell, wherein the RNA duplex contains (a) an isolated or purified miRNA consisting of miHD7A-1 (SEQ ID NO:5), miHD7A-2 (SEQ ID NO:6), miHD7B-1 (SEQ ID NO:7), or miHD7B-2 (SEQ ID NO:8); (b) a first strand of RNA and a second strand of RNA, wherein the first strand contains at least 15 contiguous nucleotides encoded by HDAS 07 (SEQ ID NO:1), HDAS 18 (SEQ ID NO:2), HDAS 19 (SEQ ID NO:3) or HDAS 20 (SEQ ID NO:4), and wherein the second strand is complementary to at least 12 contiguous nucleotides of the first strand; (c) a vector containing an expression cassettes containing a nucleic acid encoding HDAS 07 (SEQ ID NO:1), HDAS 18 (SEQ ID NO:2), HDAS 19 (SEQ ID NO:3), HDAS 20 (SEQ ID NO:4), miHD7A-1 (SEQ ID NO:5), miHD7A-2 (SEQ ID NO:6), miHD7B-1 (SEQ ID NO:7), or miHD7B-2 (SEQ ID NO:8); or (d) a vector containing a first expression cassette and a second expression cassette, wherein the first expression cassette contains a first nucleic acid encoding at least 15 contiguous nucleotides encoded by HDAS 07 (SEQ ID NO:1), HDAS 18 (SEQ ID NO:2), HDAS 19 (SEQ ID NO:3) or HDAS 20 (SEQ ID NO:4), and the second expression cassette contains a second nucleic acid encoding at least 12 contiguous nucleotides complementary to the first strand.

The present invention provides a method to inhibit expression of a huntingtin gene in a cell by introducing a ribonucleic acid (RNA) into the cell in an amount sufficient to inhibit expression of the huntingtin, and wherein the RNA duplex contains (a) an isolated or purified miRNA consisting of miHD7A-1 (SEQ ID NO:5), miHD7A-2 (SEQ ID NO:6), miHD7B-1 (SEQ ID NO:7), or miHD7B-2 (SEQ ID NO:8), or (b) a first strand of RNA and a second strand of RNA, wherein the first strand contains at least 15 contiguous nucleotides encoded by HDAS 07 (SEQ ID NO:1), HDAS 18 (SEQ ID NO:2), HDAS 19 (SEQ ID NO:3) or HDAS 20 (SEQ ID NO:4), and wherein the second strand is complementary to at least 12 contiguous nucleotides of the first strand. The huntingtin is inhibited by at least 10%, 20%, 30%, 40%, 50%, 60%, 70%, 80%, 90% 95%, or 99%.

The present invention provides a method to inhibit expression of a huntingtin gene in a mammal (e.g., a human) by (a) providing a mammal containing a neuronal cell, wherein the neuronal cell contains the huntingtin gene and the neuronal cell is susceptible to RNA interference, and the huntingtin gene is expressed in the neuronal cell; and (b) contacting the mammal with (i) an isolated or purified miRNA consisting of miHD7A-1 (SEQ ID NO:5), miHD7A-2 (SEQ ID NO:6), miHD7B-1 (SEQ ID NO:7), or miHD7B-2 (SEQ ID NO:8); (ii) a first strand of RNA and a second strand of RNA, wherein the first strand comprises at least 15 contiguous nucleotides encoded by HDAS 07 (SEQ ID NO:1), HDAS 18 (SEQ ID NO:2), HDAS 19 (SEQ ID NO:3) or HDAS 20 (SEQ ID NO:4), and wherein the second strand is complementary to at least 12 contiguous nucleotides of the first strand; (iii) a vector comprising an expression cassettes comprising a nucleic acid encoding HDAS 07 (SEQ ID NO:1), HDAS 18 (SEQ ID NO:2), HDAS 19 (SEQ ID NO:3), HDAS 20 (SEQ ID NO:4), miHD7A-1 (SEQ ID NO:5), miHD7A-2 (SEQ ID NO:6), miHD7B-1 (SEQ ID NO:7), or miHD7B-2 (SEQ ID NO:8); or (iv) a vector comprising a first expression cassette and a second expression cassette, wherein the first expression cassette comprises a first nucleic acid encoding at least 15 contiguous nucleotides encoded by HDAS 07 (SEQ ID NO:1), HDAS 18 (SEQ ID NO:2), HDAS 19 (SEQ ID NO:3) or HDAS 20 (SEQ ID NO:4), and the second expression cassette comprises a second nucleic acid encoding at least 12 contiguous nucleotides complementary to the first strand. In certain embodiments, the accumulation of huntingtin is suppressed by at least 10%. The huntingtin is inhibited by at least 10%, 20%, 30%, 40%, 50%, 60%, 70%, 80%, 90% 95%, or 99%. In certain embodiments, the cell located in vivo in a mammal.

The present invention provides a vector comprising a promoter and a micro RNA (miRNA) shuttle containing an embedded siRNA that specifically targets a target sequence associated with a condition amenable to siRNA therapy, wherein the miRNA shuttle encodes (a) an isolated first strand of RNA of 15 to 30 nucleotides in length and an isolated second strand of RNA of 15 to 30 nucleotides in length, wherein the first strand contains at least 15 contiguous nucleotides encoded by HDAS 07 (SEQ ID NO:1), HDAS 18 (SEQ ID NO:2), HDAS 19 (SEQ ID NO:3) or HDAS 20 (SEQ ID NO:4); or (b) miRNA containing miHD7A-1 (SEQ ID NO:5), miHD7A-2 (SEQ ID NO:6), miHD7B-1 (SEQ ID NO:7), or miHD7B-2 (SEQ ID NO:8). In certain embodiments, the promoter is an inducible promoter. In certain embodiments, the vector is a viral vector. In certain embodiments, the vector is an adenoviral, lentiviral, adeno-associated viral (AAV), poliovirus, HSV, or murine Maloney-based viral vector.

The present invention provides a vector containing a first expression cassette and a second expression cassette, wherein the first expression cassette contains a first nucleic acid encoding at least 15 contiguous nucleotides encoded by HDAS 07 (SEQ ID NO:1), HDAS 18 (SEQ ID NO:2), HDAS 19 (SEQ ID NO:3) or HDAS 20 (SEQ ID NO:4), and the second expression cassette contains a second nucleic acid encoding at least 12 contiguous nucleotides complementary to the first strand.

The present invention provides a method of preventing cytotoxic effects of neurodegenerative disease in a mammal in need thereof, by introducing the vector encoding a miRNA described in the preceding paragraph into a cell in an amount sufficient to suppress accumulation of a protein associated with the neurodegenerative disease, and wherein the RNA prevents cytotoxic effects of neurodegenerative disease.

The present invention also provides a method to inhibit expression of a protein associated with the neurodegenerative disease in a mammal in need thereof, by introducing the vector encoding a miRNA described above into a cell in an amount sufficient to inhibit expression of the protein associated with the neurodegenerative disease, wherein the RNA inhibits expression of the protein associated with the neurodegenerative disease. The protein associated with the neurodegenerative disease is inhibited by at least 10%, 20%, 30%, 40%, 50%, 60%, 70%, 80%, 90% 95%, or 99%.

This invention relates to compounds, compositions, and methods useful for modulating Huntington's Disease (also referred to as huntingtin, htt, or HD) gene expression using short interfering nucleic acid (siRNA) molecules. This invention also relates to compounds, compositions, and methods useful for modulating the expression and activity of other genes involved in pathways of HD gene expression and/or activity by RNA interference (RNAi) using small nucleic acid molecules. In particular, the instant invention features small nucleic acid molecules, such as short interfering nucleic acid (siRNA), short interfering RNA (siRNA), double-stranded RNA (dsRNA), micro-RNA (miRNA), and short hairpin RNA (shRNA) molecules and methods used to modulate the expression HD genes. A siRNA of the instant invention can be chemically synthesized, expressed from a vector or enzymatically synthesized.

In one embodiment, the present invention provides an AAV-1 expressed siRNA comprising an isolated first strand of RNA of 15 to 30 nucleotides in length and an isolated second strand of RNA of 15 to 30 nucleotides in length, wherein the first strand of RNA comprises at least 15 contiguous nucleotides encoded by HDAS 07 (SEQ ID NO:1), HDAS 18 (SEQ ID NO:2), HDAS 19 (SEQ ID NO:3) or HDAS 20 (SEQ ID NO:4). wherein the first or second strand comprises a sequence that is complementary to a nucleotide sequence encoding a mutant Huntington's Disease protein, wherein at least 12 nucleotides of the first and second strands are complementary to each other and form a small interfering RNA (siRNA) duplex under physiological conditions, and wherein the siRNA silences the expression of the nucleotide sequence encoding the mutant Huntington's Disease protein in the cell. In one embodiment, the first or second strand comprises a sequence that is complementary to both a mutant and wild-type Huntington's disease allele, and the siRNA silences the expression of the nucleotide sequence encoding the mutant Huntington's Disease protein and wild-type Huntington's Disease protein in the cell. In one embodiment, an AAV-1 vector of the invention is a psuedotyped rAAV-1 vector.

The present invention provides an isolated or purified miRNA consisting of miHD7A-1 (SEQ ID NO:5), miHD7A-2 (SEQ ID NO:6), miHD7B-1 (SEQ ID NO:7), or miHD7B-2 (SEQ ID NO:8).

The present invention provides a mammalian cell containing an isolated first strand of RNA of 15 to 30 nucleotides in length, and an isolated second strand of RNA of 15 to 30 nucleotides in length, wherein the first strand contains a sequence that is complementary to for example at least 15 nucleotides of RNA encoded by a targeted gene of interest (for example the HD gene), wherein for example at least 12 nucleotides of the first and second strands are complementary to each other and form a small interfering RNA (siRNA) duplex for example under physiological conditions, and wherein the siRNA silences (for example via RNA interference) only one allele of the targeted gene (for example the mutant allele of HD gene) in the cell. The duplex of the siRNA may be between 15 and 30 base pairs in length. The two strands of RNA in the siRNA may be completely complementary, or one or the other of the strands may have an "overhang region" or a "bulge region" (i.e., a portion of the RNA that does not bind with the second strand or where a portion of the RNA sequence is not complementary to the sequence of the other strand). These overhangs may be at the 3' end or at the 5' region, or at both 3' and 5' ends. Such overhang regions may be from 1 to 10 (e.g., 1, 2, 3, 4, 5, 6, 7, 8, 9, 10) or more nucleotides in length. The bulge regions may be at the ends or in the internal regions of the siRNA duplex. Such bulge regions may be from 1-5 (e.g., 1, 2, 3, 4, 5) or more nucleotides long. Such bulge regions may be the bulge regions characteristics of miRNAs. In the present invention, the first and second strand of RNA may be operably linked together by means of an RNA loop strand to form a hairpin structure to form a "duplex structure" and a "loop structure." These loop structures may be from 4 to 10 (e.g., 4, 5, 6, 7, 8, 9, 10) or more nucleotides in length. For example, the loop structure may be 4, 5 or 6 nucleotides long.

The present invention also provides a mammalian cell that contains an expression cassette encoding an isolated first strand of RNA of 15 to 30 nucleotides in length, and an isolated second strand of RNA of 15 to 30 nucleotides in length, wherein the first strand contains a sequence that is complementary to for example at least 15 contiguous nucleotides of RNA encoded by a targeted gene of interest (for example the HD gene), wherein for example at least 12 nucleotides of the first and second strands are complementary to each other and form a small interfering RNA (siRNA) duplex, for example under physiological conditions, and wherein the siRNA silences (for example via RNA interference) only one allele of the targeted gene (for example the mutant allele of HD gene) in the cell. These expression cassettes may further contain a promoter. Such promoters can be regulatable promoters or constitutive promoters. Examples of suitable promoters include a CMV, RSV, pol II or pol III promoter. The expression cassette may further contain a polyadenylation signal, such as a synthetic minimal polyadenylation signal. The expression cassette may further contain a marker gene. The expression cassette may be contained in a vector. Examples of appropriate vectors include adenoviral, lentiviral, adeno-associated viral (AAV), poliovirus, HSV, or murine Maloney-based viral vectors. In one embodiment, the vector is an adenoviral vector or an adeno-associated viral vector.

In the present invention, the alleles of the targeted gene may differ by seven or fewer nucleotides (e.g., 7, 6, 5, 4, 3, 2 or 1 nucleotides). For example the alleles may differ by only one nucleotide. Examples of targeted gene transcripts include transcripts encoding a beta-glucuronidase, TorsinA, Ataxin-3, Tau, or huntingtin. The targeted genes and gene products (i.e., a transcript or protein) may be from different species of organisms, such as a mouse allele or a human allele of a target gene.

The RNA duplexes of the present invention are between 15 and 30 base pairs in length. For example they may be between 19 and 25 base pairs in length or 19-27 base-pairs in length. As discussed above the first and/or second strand further may optionally comprise an overhang region. These overhangs may be at the 3' end or at the 5' overhang region, or at both 3' and 5' ends. Such overhang regions may be from 1 to 10 nucleotides in length. The RNA duplex of the present invention may optionally include nucleotide bulge regions. The bulge regions may be at the ends or in the internal regions of the siRNA duplex. Such bulge regions may be from 1-5 nucleotides long. Such bulge regions may be the bulge regions characteristics of miRNAs. In the present invention, the first and second strand of RNA may be operably linked together by means of an RNA loop strand to form a hairpin structure to form a "duplex structure" and a "loop structure." These loop structures may be from 4 to 10 nucleotides in length. For example, the loop structure may be 4, 5 or 6 nucleotides long.

In the present invention, an expression cassette may contain a nucleic acid encoding at least one strand of the RNA duplex described above. Such an expression cassette may further contain a promoter. The expression cassette may be contained in a vector. These cassettes and vectors may be contained in a cell, such as a mammalian cell. A non-human mammal may contain the cassette or vector. The vector may contain two expression cassettes, the first expression cassette containing a nucleic acid encoding the first strand of the RNA duplex, and a second expression cassette containing a nucleic acid encoding the second strand of the RNA duplex.

In one embodiment, the present invention further provides a method of performing gene silencing in a mammal or mammalian cell by administering to the mammal an isolated first strand of RNA of about 15 to about 30 nucleotides (for example 19-27 nucleotides) in length, and an isolated second strand of RNA of 15 to 30 nucleotides (for example 19-27 nucleotides) in length, wherein the first strand contains for example at least 15 contiguous nucleotides complementary to a targeted gene of interest (such as HD gene), wherein for example at least 12 nucleotides of the first and second strands are complementary to each other and form a small interfering RNA (siRNA) duplex for example under physiological conditions, and wherein the siRNA silences only one or both alleles of the targeted gene (for example the wild type and mutant alleles of HD gene) in the mammal or mammalian cell. In one example, the gene is a beta-glucuronidase gene. The alleles may be murine-specific and human-specific alleles of beta-glucuronidase. Examples of gene transcripts include an RNA transcript complementary to TorsinA, Ataxin-3, huntingtin or Tau. The targeted gene may be a gene associated with a condition amenable to siRNA therapy. For example, the condition amenable to siRNA therapy could be a disabling neurological disorder.

"Neurological disease" and "neurological disorder" refer to both hereditary and sporadic conditions that are characterized by nervous system dysfunction, and which may be associated with atrophy of the affected central or peripheral nervous system structures, or loss of function without atrophy. A neurological disease or disorder that results in atrophy is commonly called a "neurodegenerative disease" or "neurodegenerative disorder." Neurodegenerative diseases and disorders include, but are not limited to, amyotrophic lateral sclerosis (ALS), hereditary spastic hemiplegia, primary lateral sclerosis, spinal muscular atrophy, Kennedy's disease, Alzheimer's disease, Parkinson's disease, multiple sclerosis, and repeat expansion neurodegenerative diseases, e.g., diseases associated with expansions of trinucleotide repeats such as polyglutamine (polyQ) repeat diseases, e.g., Huntington's disease (HD), spinocerebellar ataxia (SCA1, SCA2, SCA3, SCA6, SCAT, and SCA17), spinal and bulbar muscular atrophy (SBMA), dentatorubropallidoluysian atrophy (DRPLA). An example of a disabling neurological disorder that does not appear to result in atrophy is DYT1 dystonia. The gene of interest may encode a ligand for a chemokine involved in the migration of a cancer cell, or a chemokine receptor.

The present invention further provides a method of substantially silencing a target gene of interest or targeted allele for the gene of interest in order to provide a therapeutic effect. As used herein the term "substantially silencing" or "substantially silenced" refers to decreasing, reducing, or inhibiting the expression of the target gene or target allele by at least about 5%, 10%, 15%, 20%, 25%, 30%, 35%, 40%, 45%, 50%, 55%, 60%, 65%, 70%, 75%, 80%, 85% to 100%. As used herein the term "therapeutic effect" refers to a change in the associated abnormalities of the disease state, including pathological and behavioral deficits; a change in the time to progression of the disease state; a reduction, lessening, or alteration of a symptom of the disease; or an improvement in the quality of life of the person afflicted with the disease. Therapeutic effect can be measured quantitatively by a physician or qualitatively by a patient afflicted with the disease state targeted by the siRNA. In certain embodiments wherein both the mutant and wild type allele are substantially silenced, the term therapeutic effect defines a condition in which silencing of the wild type allele's expression does not have a deleterious or harmful effect on normal functions such that the patient would not have a therapeutic effect.

In one embodiment, the present invention further provides a method of performing allele-specific gene silencing in a mammal by administering to the mammal an isolated first strand of RNA of 15 to 30 nucleotides in length, and an isolated second strand of RNA of 15 to 30 nucleotides in length, wherein the first strand contains for example at least 15 contiguous nucleotides complementary to a targeted gene of interest, wherein for example at least 12 nucleotides of the first and second strands are complementary to each other and form a small interfering RNA (siRNA) duplex for example under physiological conditions, and wherein the siRNA silences only one allele of the targeted gene in the mammal. The alleles of the gene may differ by seven or fewer base pairs, such as by only one base pair. In one example, the gene is a beta-glucuronidase gene. The alleles may be murine-specific and human-specific alleles of beta-glucuronidase. Examples of gene transcripts include an RNA transcript complementary to TorsinA, Ataxin-3, huntingtin or Tau. The targeted gene may be a gene associated with a condition amenable to siRNA therapy. For example, the condition amenable to siRNA therapy could be a disabling neurological disorder.

"Neurological disease" and "neurological disorder" refer to both hereditary and sporadic conditions that are characterized by nervous system dysfunction, and which may be associated with atrophy of the affected central or peripheral nervous system structures, or loss of function without atrophy. A neurological disease or disorder that results in atrophy is commonly called a "neurodegenerative disease" or "neurodegenerative disorder." Neurodegenerative diseases and disorders include, but are not limited to, amyotrophic lateral sclerosis (ALS), hereditary spastic hemiplegia, primary lateral sclerosis, spinal muscular atrophy, Kennedy's disease, Alzheimer's disease, Parkinson's disease, multiple sclerosis, and repeat expansion neurodegenerative diseases, e.g., diseases associated with expansions of trinucleotide repeats such as polyglutamine (polyQ) repeat diseases, e.g., Huntington's disease (HD), spinocerebellar ataxia (SCA1, SCA2, SCA3, SCA6, SCA7, and SCA17), spinal and bulbar muscular atrophy (SBMA), dentatorubropallidoluysian atrophy (DRPLA). An example of a disabling neurological disorder that does not appear to result in atrophy is DYT1 dystonia. The gene of interest may encode a ligand for a chemokine involved in the migration of a cancer cell, or a chemokine receptor.

In one embodiment, the present invention further provides a method of substantially silencing both alleles (e.g., both mutant and wild type alleles) of a target gene. In certain embodiments, the targeting of both alleles of a gene target of interest can confer a therapeutic effect by allowing a certain level of continued expression of the wild-type allele while at the same time inhibiting expression of the mutant (e.g., disease associated) allele at a level that provides a therapeutic effect. For example, a therapeutic effect can be achieved by conferring on the cell the ability to express siRNA as an expression cassette, wherein the expression cassette contains a nucleic acid encoding a small interfering RNA molecule (siRNA) targeted against both alleles, and wherein the expression of the targeted alleles are silenced at a level that inhibits, reduces, or prevents the deleterious gain of function conferred by the mutant allele, but that still allows for adequate expression of the wild type allele at a level that maintains the function of the wild type allele. Examples of such wild type and mutant alleles include without limitation those associated with polyglutamine diseases such as Huntington's Disease.

In one embodiment, the present invention further provides a method of substantially silencing a target allele while allowing expression of a wild-type allele by conferring on the cell the ability to express siRNA as an expression cassette, wherein the expression cassette contains a nucleic acid encoding a small interfering RNA molecule (siRNA) targeted against a target allele, wherein expression from the targeted allele is substantially silenced but wherein expression of the wild-type allele is not substantially silenced.

In one embodiment, the present invention provides a method of treating a dominantly inherited disease in an allele-specific manner by administering to a patient in need thereof an expression cassette, wherein the expression cassette contains a nucleic acid encoding a small interfering RNA molecule (siRNA) targeted against a target allele, wherein expression from the target allele is substantially silenced but wherein expression of the wild-type allele is not substantially silenced.

In one embodiment, the present invention provides a method of treating a dominantly inherited disease by administering to a patient in need thereof an expression cassette, wherein the expression cassette contains a nucleic acid encoding a small interfering RNA molecule (siRNA) targeted against both the mutant allele and the wild type allele of the target gene, wherein expression from the mutant allele is substantially silenced at a level that still allows for expression from the wild type allele to maintain its function in the patient.

In one embodiment, the present invention also provides a method of performing allele-specific gene silencing by administering an expression cassette containing a pol II promoter operably-linked to a nucleic acid encoding at least one strand of a small interfering RNA molecule (siRNA) targeted against a gene of interest, wherein the siRNA silences only one allele of a gene.

In one embodiment, the present invention also provides a method of performing gene silencing by administering an expression cassette containing a pol II promoter operably-linked to a nucleic acid encoding at least one strand of a small interfering RNA molecule (siRNA) targeted against a gene of interest, wherein the siRNA silences one or both alleles of the gene.

In one embodiment, the present invention provides a method of performing allele-specific gene silencing in a mammal by administering to the mammal a vector containing an expression cassette, wherein the expression cassette contains a nucleic acid encoding at least one strand of a small interfering RNA molecule (siRNA) targeted against a gene of interest, wherein the siRNA silences only one allele of a gene.

In one embodiment, the present invention provides a method of performing gene silencing in a mammal by administering to the mammal a vector containing an expression cassette, wherein the expression cassette contains a nucleic acid encoding at least one strand of a small interfering RNA molecule (siRNA) targeted against a gene of interest, wherein the siRNA silences one or both alleles of the gene.

In one embodiment, the present invention provides a method of screening of allele-specific siRNA duplexes, involving contacting a cell containing a predetermined mutant allele with an siRNA with a known sequence, contacting a cell containing a wild-type allele with an siRNA with a known sequence, and determining if the mutant allele is substantially silenced while the wild-type allele retains substantially normal activity.

In one embodiment, the present invention provides a method of screening of specific siRNA duplexes, involving contacting a cell containing both a predetermined mutant allele and a predetermined wild-type allele with an siRNA with a known sequence, and determining if the mutant allele is substantially silenced at a level that allows the wild-type allele to retain substantially normal activity.

In one embodiment, the present invention also provides a method of screening of allele-specific siRNA duplexes involving contacting a cell containing a predetermined mutant allele and a wild-type allele with an siRNA with a known sequence, and determining if the mutant allele is substantially silenced while the wild-type allele retains substantially normal activity.

In one embodiment, the present invention also provides a method for determining the function of an allele by contacting a cell containing a predetermined allele with an siRNA with a known sequence, and determining if the function of the allele is substantially modified.

In one embodiment, the present invention further provides a method for determining the function of an allele by contacting a cell containing a predetermined mutant allele and a wild-type allele with an siRNA with a known sequence, and determining if the function of the allele is substantially modified while the wild-type allele retains substantially normal function.

In one embodiment, the invention features a method for treating or preventing Huntington's Disease in a subject or organism comprising contacting the subject or organism with a siRNA of the invention under conditions suitable to modulate the expression of the HD gene in the subject or organism whereby the treatment or prevention of Huntington's Disease can be achieved. In one embodiment, the HD gene target comprises a mutant HD allele (e.g., an allele comprising a trinucleotide (CAG) repeat expansion). In one embodiment, the HD gene target comprises both HD allele (e.g., an allele comprising a trinucleotide (CAG) repeat expansion and a wild type allele). The siRNA molecule of the invention can be expressed from vectors as described herein or otherwise known in the art to target appropriate tissues or cells in the subject or organism.

In one embodiment, the invention features a method for treating or preventing Huntington's Disease in a subject or organism comprising, contacting the subject or organism with a siRNA molecule of the invention via local administration to relevant tissues or cells, such as brain cells and tissues (e.g., basal ganglia, striatum, or cortex), for example, by administration of vectors or expression cassettes of the invention that provide siRNA molecules of the invention to relevant cells (e.g., basal ganglia, striatum, or cortex). In one embodiment, the siRNA, vector, or expression cassette is administered to the subject or organism by stereotactic or convection enhanced delivery to the brain. For example, U.S. Pat. No. 5,720,720 provides methods and devices useful for stereotactic and convection enhanced delivery of reagents to the brain. Such methods and devices can be readily used for the delivery of siRNAs, vectors, or expression cassettes of the invention to a subject or organism, and is incorporated by reference herein in its entirety. US Patent Application Nos. 2002/0141980; 2002/0114780; and 2002/0187127 all provide methods and devices useful for stereotactic and convection enhanced delivery of reagents that can be readily adapted for delivery of siRNAs, vectors, or expression cassettes of the invention to a subject or organism, and are incorporated by reference herein in their entireties. Particular devices that may be useful in delivering siRNAs, vectors, or expression cassettes of the invention to a subject or organism are for example described in US Patent Application No. 2004/0162255, which is incorporated by reference herein in its entirety. The siRNA molecule of the invention can be expressed from vectors as described herein or otherwise known in the art to target appropriate tissues or cells in the subject or organism.

In one embodiment, a viral vector of the invention is an AAV vector. An "AAV" vector refers to an adeno-associated virus, and may be used to refer to the naturally occurring wild-type virus itself or derivatives thereof. The term covers all subtypes, serotypes and pseudotypes, and both naturally occurring and recombinant forms, except where required otherwise. As used herein, the term "serotype" refers to an AAV which is identified by and distinguished from other AAVs based on capsid protein reactivity with defined antisera, e.g., there are eight known serotypes of primate AAVs, AAV-1 to AAV-8. For example, serotype AAV-2 is used to refer to an AAV which contains capsid proteins encoded from the cap gene of AAV-2 and a genome containing 5' and 3' ITR sequences from the same AAV-2 serotype. Pseudotyped AAV refers to an AAV that contains capsid proteins from one serotype and a viral genome including 5'-3' ITRs of a second serotype. Pseudotyped rAAV would be expected to have cell surface binding properties of the capsid serotype and genetic properties consistent with the ITR serotype. Pseudotyped rAAV are produced using standard techniques described in the art. As used herein, for example, rAAV1 may be used to refer an AAV having both capsid proteins and 5'-3' ITRs from the same serotype or it may refer to an AAV having capsid proteins from serotype 1 and 5'-3' ITRs from a different AAV serotype, e.g., AAV serotype 2. For each example illustrated herein the description of the vector design and production describes the serotype of the capsid and 5'-3' ITR sequences. The abbreviation "rAAV" refers to recombinant adeno-associated virus, also referred to as a recombinant AAV vector (or "rAAV vector").

An "AAV virus" or "AAV viral particle" refers to a viral particle composed of at least one AAV capsid protein (preferably by all of the capsid proteins of a wild-type AAV) and an encapsidated polynucleotide. If the particle comprises heterologous polynucleotide (i.e., a polynucleotide other than a wild-type AAV genome such as a transgene to be delivered to a mammalian cell), it is typically referred to as "rAAV."

In one embodiment, the AAV expression vectors are constructed using known techniques to at least provide as operatively linked components in the direction of transcription, control elements including a transcriptional initiation region, the DNA of interest and a transcriptional termination region. The control elements are selected to be functional in a mammalian cell. The resulting construct which contains the operatively linked components is flanked (5' and 3') with functional AAV ITR sequences.

By "adeno-associated virus inverted terminal repeats" or "AAV ITRs" is meant the art-recognized regions found at each end of the AAV genome which function together in cis as origins of DNA replication and as packaging signals for the virus. AAV ITRs, together with the AAV rep coding region, provide for the efficient excision and rescue from, and integration of a nucleotide sequence interposed between two flanking ITRs into a mammalian cell genome.

The nucleotide sequences of AAV ITR regions are known. As used herein, an "AAV ITR" need not have the wild-type nucleotide sequence depicted, but may be altered, e.g., by the insertion, deletion or substitution of nucleotides. Additionally, the AAV ITR may be derived from any of several AAV serotypes, including without limitation, AAV-1, AAV-2, AAV-3, AAV-4, AAV-5, AAVX7, etc. Furthermore, 5' and 3' ITRs which flank a selected nucleotide sequence in an AAV vector need not necessarily be identical or derived from the same AAV serotype or isolate, so long as they function as intended, i.e., to allow for excision and rescue of the sequence of interest from a host cell genome or vector, and to allow integration of the heterologous sequence into the recipient cell genome when AAV Rep gene products are present in the cell.

In one embodiment, AAV ITRs can be derived from any of several AAV serotypes, including without limitation, AAV-1, AAV-2, AAV-3, AAV-4, AAV-5, AAVX7, etc. Furthermore, 5' and 3' ITRs which flank a selected nucleotide sequence in an AAV expression vector need not necessarily be identical or derived from the same AAV serotype or isolate, so long as they function as intended, i.e., to allow for excision and rescue of the sequence of interest from a host cell genome or vector, and to allow integration of the DNA molecule into the recipient cell genome when AAV Rep gene products are present in the cell.

In one embodiment, AAV capsids can be derived from any of several AAV serotypes, including without limitation, AAV-1, AAV-2, AAV-3, AAV-4, AAV-5, AAV6, or AAV8, and the AAV ITRS are derived form AAV serotype 2. Suitable DNA molecules for use in AAV vectors will be less than about 5 kilobases (kb), less than about 4.5 kb, less than about 4 kb, less than about 3.5 kb, less than about 3 kb, less than about 2.5 kb in size. In some embodiments of the invention the DNA molecules for use in the AAV vectors will contain multiple copies of the identical siRNA sequence. As used herein the term multiple copies of an siRNA sequences means at least 2 copies, at least 3 copies, at least 4 copies, at least 5 copies, at least 6 copies, at least 7 copies, at least 8 copies, at least 9 copies, and at least 10 copies. In some embodiments the DNA molecules for use in the AAV vectors will contain multiple siRNA sequences. As used herein the term "multiple siRNA sequences" means at least two siRNA sequences, at least three siRNA sequences, at least four siRNA sequences, at least five siRNA sequences, at least six siRNA sequences, at least seven siRNA sequences, at least eight siRNA sequences, at least nine siRNA sequences, and at least ten siRNA sequences. In some embodiments suitable DNA vectors of the invention will contain a sequence encoding the siRNA molecule of the invention and a stuffer fragment. Suitable stuffer fragments of the invention include sequences known in the art including without limitation sequences which do not encode an expressed protein molecule; sequences which encode a normal cellular protein which would not have deleterious effect on the cell types in which it was expressed; and sequences which would not themselves encode a functional siRNA duplex molecule.

In one embodiment, suitable DNA molecules for use in AAV vectors will be less than about 5 kilobases (kb) in size and will include, for example, a stuffer sequence and a sequence encoding a siRNA molecule of the invention. For example, in order to prevent any packaging of AAV genomic sequences containing the rep and cap genes, a plasmid containing the rep and cap DNA fragment may be modified by the inclusion of a stuffer fragment as is known in the art into the AAV genome which causes the DNA to exceed the length for optimal packaging. Thus, the helper fragment is not packaged into AAV virions. This is a safety feature, ensuring that only a recombinant AAV vector genome that does not exceed optimal packaging size is packaged into virions. An AAV helper fragment that incorporates a stuffer sequence can exceed the wild-type genome length of 4.6 kb, and lengths above 105% of the wild-type will generally not be packaged. The stuffer fragment can be derived from, for example, such non-viral sources as the Lac-Z or beta-galactosidase gene.

In one embodiment, the selected nucleotide sequence is operably linked to control elements that direct the transcription or expression thereof in the subject in vivo. Such control elements can comprise control sequences normally associated with the selected gene. Alternatively, heterologous control sequences can be employed. Useful heterologous control sequences generally include those derived from sequences encoding mammalian or viral genes. Examples include, but are not limited to, the SV40 early promoter, mouse mammary tumor virus LTR promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, pol II promoters, pol III promoters, synthetic promoters, hybrid promoters, and the like. In addition, sequences derived from nonviral genes, such as the murine metallothionein gene, will also find use herein. Such promoter sequences are commercially available from, e.g., Stratagene® (San Diego, Calif.).

In one embodiment, both heterologous promoters and other control elements, such as CNS-specific and inducible promoters, enhancers and the like, will be of particular use. Examples of heterologous promoters include the CMB promoter. Examples of CNS-specific promoters include those isolated from the genes from myelin basic protein (MBP), glial fibrillary acid protein (GFAP), and neuron specific enolase (NSE). Examples of inducible promoters include DNA responsive elements for ecdysone, tetracycline, hypoxia and aufin.

In one embodiment, the AAV expression vector which harbors the DNA molecule of interest bounded by AAV ITRs, can be constructed by directly inserting the selected sequence(s) into an AAV genome which has had the major AAV open reading frames ("ORFs") excised therefrom. Other portions of the AAV genome can also be deleted, so long as a sufficient portion of the ITRs remain to allow for replication and packaging functions. Such constructs can be designed using techniques well known in the art. See, e.g., U.S. Pat. Nos. 5,173,414 and 5,139,941.

Alternatively, AAV ITRs can be excised from the viral genome or from an AAV vector containing the same and fused 5' and 3' of a selected nucleic acid construct that is present in another vector using standard ligation techniques, such as those described in Sambrook and Russell, *Molecular Cloning: A Laboratory Manual*, Cold Spring Harbor Laboratory Press Cold Spring Harbor, N.Y. (2001). For example, ligations can be accomplished in 20 mM Tris-Cl pH 7.5, 10 mM $MgCl_2$, 10 mM DTT, 33 µg/ml BSA, 10 mM-50 mM NaCl, and either 40 µM ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 30-100 µg/ml total DNA concentrations (5-100 nM total end concentration). AAV vectors which contain ITRs have been described in, e.g., U.S. Pat. No. 5,139,941. In particular, several AAV vectors are described therein which are available from the American Type Culture Collection ("ATCC") under Accession Numbers 53222, 53223, 53224, 53225 and 53226.

Additionally, chimeric genes can be produced synthetically to include AAV ITR sequences arranged 5' and 3' of one or more selected nucleic acid sequences. Preferred codons for expression of the chimeric gene sequence in mammalian CNS cells can be used. The complete chimeric sequence is assembled from overlapping oligonucleotides prepared by standard methods.

In order to produce rAAV virions, an AAV expression vector is introduced into a suitable host cell using known techniques, such as by transfection. A number of transfection techniques are generally known in the art. Particularly suitable transfection methods include calcium phosphate co-precipitation, direct microinjection into cultured cells, electroporation, liposome mediated gene transfer, lipid-mediated transduction, and nucleic acid delivery using high-velocity microprojectiles.

In one embodiment, suitable host cells for producing rAAV virions include microorganisms, yeast cells, insect cells, and mammalian cells, that can be, or have been, used as recipients of a heterologous DNA molecule. The term includes the progeny of the original cell which has been transfected. Thus, a "host cell" as used herein generally refers to a cell which has been transfected with an exogenous DNA sequence. Cells from the stable human cell line, 293 (readily available through, e.g., the American Type Culture Collection under Accession Number ATCC CRL1573) can be used in the practice of the present invention. Particularly, the human cell line 293 is a human embryonic kidney cell line that has been transformed with adenovirus type-5 DNA fragments, and expresses the adenoviral E1a and E1b genes. The 293 cell line is readily transfected, and provides a particularly convenient platform in which to produce rAAV virions.

In one embodiment, host cells containing the above-described AAV expression vectors are rendered capable of providing AAV helper functions in order to replicate and encapsidate the nucleotide sequences flanked by the AAV ITRs to produce rAAV virions. AAV helper functions are generally AAV-derived coding sequences which can be expressed to provide AAV gene products that, in turn, function in trans for productive AAV replication. AAV helper functions are used herein to complement necessary AAV functions that are missing from the AAV expression vectors. Thus, AAV helper functions include one, or both of the major AAV ORFs, namely the rep and cap coding regions, or functional homologues thereof.

The Rep expression products have been shown to possess many functions, including, among others: recognition, binding and nicking of the AAV origin of DNA replication; DNA helicase activity; and modulation of transcription from AAV (or other heterologous) promoters. The Cap expression products supply necessary packaging functions. AAV helper functions are used herein to complement AAV functions in trans that are missing from AAV vectors.

The term "AAV helper construct" refers generally to a nucleic acid molecule that includes nucleotide sequences providing AAV functions deleted from an AAV vector which is to be used to produce a transducing vector for delivery of a nucleotide sequence of interest. AAV helper constructs are commonly used to provide transient expression of AAV rep and/or cap genes to complement missing AAV functions that are necessary for lytic AAV replication; however, helper constructs lack AAV ITRs and can neither replicate nor package themselves. AAV helper constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products.

By "AAV rep coding region" is meant the art-recognized region of the AAV genome which encodes the replication proteins Rep 78, Rep 68, Rep 52 and Rep 40. These Rep expression products have been shown to possess many functions, including recognition, binding and nicking of the AAV origin of DNA replication, DNA helicase activity and modulation of transcription from AAV (or other heterologous) promoters. The Rep expression products are collectively required for replicating the AAV genome. Suitable homologues of the AAV rep coding region include the human herpesvirus 6 (HHV-6) rep gene which is also known to mediate AAV-2 DNA replication.

By "AAV cap coding region" is meant the art-recognized region of the AAV genome which encodes the capsid proteins VP1, VP2, and VP3, or functional homologues thereof. These Cap expression products supply the packaging functions which are collectively required for packaging the viral genome.

In one embodiment, AAV helper functions are introduced into the host cell by transfecting the host cell with an AAV helper construct either prior to, or concurrently with, the transfection of the AAV expression vector. AAV helper constructs are thus used to provide at least transient expression of AAV rep and/or cap genes to complement missing AAV functions that are necessary for productive AAV infection. AAV helper constructs lack AAV ITRs and can neither replicate nor package themselves. These constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products.

In one embodiment, both AAV expression vectors and AAV helper constructs can be constructed to contain one or more optional selectable markers. Suitable markers include genes which confer antibiotic resistance or sensitivity to, impart color to, or change the antigenic characteristics of those cells which have been transfected with a nucleic acid construct containing the selectable marker when the cells are grown in an appropriate selective medium. Several selectable marker genes that are useful in the practice of the invention include the hygromycin B resistance gene (encoding Aminoglycoside phosphotranferase (APH)) that allows selection in mammalian cells by conferring resistance to G418 (available from Sigma, St. Louis, Mo.). Other suitable markers are known to those of skill in the art.

In one embodiment, the host cell (or packaging cell) is rendered capable of providing non AAV derived functions, or "accessory functions," in order to produce rAAV virions. Accessory functions are non AAV derived viral and/or cellular functions upon which AAV is dependent for its replication. Thus, accessory functions include at least those non AAV proteins and RNAs that are required in AAV replication, including those involved in activation of AAV gene transcription, stage specific AAV mRNA splicing, AAV DNA replication, synthesis of Cap expression products and AAV capsid assembly. Viral-based accessory functions can be derived from any of the known helper viruses.

In one embodiment, accessory functions can be introduced into and then expressed in host cells using methods known to those of skill in the art. Commonly, accessory functions are provided by infection of the host cells with an unrelated helper virus. A number of suitable helper viruses are known, including adenoviruses; herpesviruses such as herpes simplex virus types 1 and 2; and vaccinia viruses. Nonviral accessory functions will also find use herein, such as those provided by cell synchronization using any of various known agents.

In one embodiment, accessory functions are provided using an accessory function vector. Accessory function vectors include nucleotide sequences that provide one or more accessory functions. An accessory function vector is capable of being introduced into a suitable host cell in order to support efficient AAV virion production in the host cell. Accessory function vectors can be in the form of a plasmid, phage, transposon or cosmid. Accessory vectors can also be in the form of one or more linearized DNA or RNA fragments which, when associated with the appropriate control elements and enzymes, can be transcribed or expressed in a host cell to provide accessory functions.

In one embodiment, nucleic acid sequences providing the accessory functions can be obtained from natural sources, such as from the genome of an adenovirus particle, or constructed using recombinant or synthetic methods known in the art. In this regard, adenovirus-derived accessory functions have been widely studied, and a number of adenovirus genes involved in accessory functions have been identified and partially characterized. Specifically, early adenoviral gene regions E1a, E2a, E4, VAI RNA and, possibly, E1b are thought to participate in the accessory process. Herpesvirus-derived accessory functions have been described. Vaccinia virus-derived accessory functions have also been described.

In one embodiment, as a consequence of the infection of the host cell with a helper virus, or transfection of the host cell with an accessory function vector, accessory functions are expressed which transactivate the AAV helper construct to produce AAV Rep and/or Cap proteins. The Rep expression products excise the recombinant DNA (including the DNA of interest) from the AAV expression vector. The Rep proteins also serve to duplicate the AAV genome. The expressed Cap proteins assemble into capsids, and the recombinant AAV genome is packaged into the capsids. Thus, productive AAV replication ensues, and the DNA is packaged into rAAV virions.

In one embodiment, following recombinant AAV replication, rAAV virions can be purified from the host cell using a variety of conventional purification methods, such as CsCl gradients. Further, if infection is employed to express the accessory functions, residual helper virus can be inactivated, using known methods. For example, adenovirus can be inactivated by heating to temperatures of approximately 60.degrees C. for, e.g., 20 minutes or more. This treatment effectively inactivates only the helper virus since AAV is extremely heat stable while the helper adenovirus is heat labile. The resulting rAAV virions are then ready for use for DNA delivery to the CNS (e.g., cranial cavity) of the subject.

Methods of delivery of viral vectors include, but are not limited to, intra-arterial, intra-muscular, intravenous, intranasal and oral routes. Generally, rAAV virions may be introduced into cells of the CNS using either in vivo or in vitro transduction techniques. If transduced in vitro, the desired recipient cell will be removed from the subject, transduced with rAAV virions and reintroduced into the subject. Alternatively, syngeneic or xenogeneic cells can be used where those cells will not generate an inappropriate immune response in the subject.

Suitable methods for the delivery and introduction of transduced cells into a subject have been described. For example, cells can be transduced in vitro by combining recombinant AAV virions with CNS cells e.g., in appropriate media, and screening for those cells harboring the DNA of interest can be screened using conventional techniques such as Southern blots and/or PCR, or by using selectable markers. Transduced cells can then be formulated into pharmaceutical compositions, described more fully below, and the composition introduced into the subject by various techniques, such as by grafting, intramuscular, intravenous, subcutaneous and intraperitoneal injection.

In one embodiment, for in vivo delivery, the rAAV virions are formulated into pharmaceutical compositions and will generally be administered parenterally, e.g., by intramuscular injection directly into skeletal or cardiac muscle or by injection into the CNS.

In one embodiment, viral vectors of the invention are delivered to the CNS via convection-enhanced delivery (CED) systems that can efficiently deliver viral vectors, e.g., AAV, over large regions of a subject's brain (e.g., striatum and/or cortex). As described in detail and exemplified below, these methods are suitable for a variety of viral vectors, for instance AAV vectors carrying therapeutic genes (e.g., siRNAs).

Any convection-enhanced delivery device may be appropriate for delivery of viral vectors. In one embodiment, the device is an osmotic pump or an infusion pump. Both osmotic and infusion pumps are commercially available from a variety of suppliers, for example Alzet Corporation, Hamilton Corporation, Aiza, Inc., Palo Alto, Calif.). Typically, a viral vector is delivered via CED devices as follows. A catheter, cannula or other injection device is inserted into CNS tissue in the chosen subject. In view of the teachings herein, one of skill in the art could readily determine which general area of the CNS is an appropriate target. For example, when delivering AAV vector encoding a therapeutic gene to treat PD, the striatum is a suitable area of the brain to target. Stereotactic maps and positioning devices are available, for example from ASI Instruments, Warren, Mich. Positioning may also be conducted by using anatomical maps obtained by CT and/or MRI imaging of the subject's brain to help guide the injection device to the chosen target. Moreover, because the methods described herein can be practiced such that relatively large areas of the brain take up the viral vectors, fewer infusion cannula are needed. Since surgical complications are related to the number of penetrations, the methods described herein also serve to reduce the side effects seen with conventional delivery techniques.

In one embodiment, pharmaceutical compositions will comprise sufficient genetic material to produce a therapeutically effective amount of the siRNA of interest, i.e., an amount sufficient to reduce or ameliorate symptoms of the disease state in question or an amount sufficient to confer the desired benefit. The pharmaceutical compositions will also contain a pharmaceutically acceptable excipient. Such excipients include any pharmaceutical agent that does not itself induce the production of antibodies harmful to the individual receiving the composition, and which may be administered without undue toxicity. Pharmaceutically acceptable excipients include, but are not limited to, sorbitol, Tween80, and liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in REMINGTON'S PHARMACEUTICAL SCIENCES (Mack Pub. Co., N.J. 1991).

As is apparent to those skilled in the art in view of the teachings of this specification, an effective amount of viral vector which must be added can be empirically determined. Administration can be effected in one dose, continuously or intermittently throughout the course of treatment. Methods of determining the most effective means and dosages of administration are well known to those of skill in the art and will vary with the viral vector, the composition of the therapy, the target cells, and the subject being treated. Single and multiple administrations can be carried out with the dose level and pattern being selected by the treating physician.

It should be understood that more than one transgene could be expressed by the delivered viral vector. Alternatively, separate vectors, each expressing one or more different transgenes, can also be delivered to the CNS as described herein. Furthermore, it is also intended that the viral vectors delivered by the methods of the present invention be combined with other suitable compositions and therapies.

BRIEF DESCRIPTION OF THE FIGURES

FIGS. 1A and 1B. Targeting mutant huntingtin. FIG. 1A provides a schematic representation of the huntingtin (htt) gene. The intron sequences are the lightest bands, and the exon sequences are the second lightest bands. The expanded CAG sequence (dark band) is localized in the first exon of the Htt gene. FIG. 1B provides siRNA walking 5' and 3'. Sequences of short interfering RNA (siRNA) targeting 5' and 3' of the CAG-repeat region were generated to preferentially target the mutant huntingtin allele.

FIGS. 2A and 2B. Constructs to assess allele-specific silencing. Two plasmids were generated expressing full-length wild type (FIG. 2A, pCMV-FLHtt 18Q-Flag) or mutant huntingtin (FIG. 2B, pCMV-FLHtt 83Q-V5).

FIG. 3A shows wild type Htt and FIG. 3B shows mutant Htt. As seen in FIG. 3C, siRNA sequence number 7 (S7) reduced mutant htt by 40% and the wild type huntingtin by 6%.

FIG. 5A shows normal Htt, and FIG. 5B shows mutant Htt.

DETAILED DESCRIPTION OF THE INVENTION

Figure 3C:
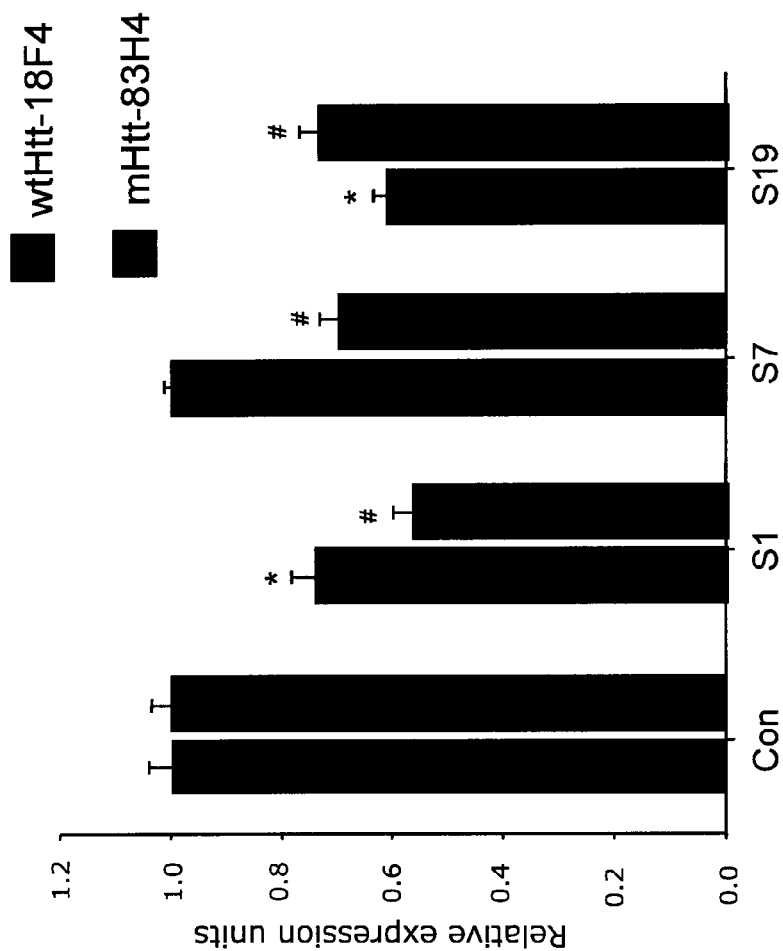
FIGS. 3A-3C shows Western blots and Q-PCR results for candidate siRNA sequences.

Modulation of gene expression by endogenous, noncoding RNAs is increasingly appreciated as a mechanism playing a role in eukaryotic development, maintenance of chromatin structure and genomic integrity. Recently, techniques have been developed to trigger RNA interference (RNAi) against specific targets in mammalian cells by introducing exogenously produced or intracellularly expressed siRNAs. These methods have proven to be quick, inexpensive and effective for knockdown experiments in vitro and in vivo. The ability to accomplish selective gene silencing has led to the hypothesis that siRNAs might be employed to suppress gene expression for therapeutic benefit.

RNA interference is now established as an important biological strategy for gene silencing, but its application to mammalian cells has been limited by nonspecific inhibitory effects of long double-stranded RNA on translation. Moreover, delivery of interfering RNA has largely been limited to administration of RNA molecules. Hence, such administration must be performed repeatedly to have any sustained effect. The present inventors have developed a delivery mechanism that results in specific silencing of targeted genes through expression of small interfering RNA (siRNA). The inventors have markedly diminished expression of exogenous and endogenous genes in vitro and in vivo and apply this novel strategy to a model system of a major class of neurodegenerative disorders, the polyglutamine diseases, to show reduced polyglutamine aggregation in cells. This strategy is generally useful in reducing expression of target genes in order to model biological processes or to provide therapy for dominant human diseases.

Disclosed herein is a strategy that results in substantial silencing of targeted alleles via siRNA. Use of this strategy results in markedly diminished in vitro and in vivo expression of targeted alleles. This strategy is useful in reducing expression of targeted alleles in order to model biological processes or to provide therapy for human diseases. For example, this strategy can be applied to a major class of neurodegenerative disorders, the polyglutamine diseases, as is demonstrated by the reduction of polyglutamine aggregation in cells following application of the strategy. As used herein the term "substantial silencing" means that the mRNA of the targeted allele is inhibited and/or degraded by the presence of the introduced siRNA, such that expression of the targeted allele is reduced by about 10% to 100% as compared to the level of expression seen when the siRNA is not present. Generally, when an allele is substantially silenced, it will have at least 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, 98%, 99% or even 100% reduction expression as compared to when the siRNA is not present. As used herein the term "substantially normal activity" means the level of expression of an allele when an siRNA has not been introduced to a cell.

Dominantly inherited diseases, including polyQ neurodegenerative disorders, are ideal candidates for siRNA-based therapy. The polyQ neurodegenerative disorders include at least nine inherited disorders caused by CAG repeat expansions that encode polyQ in the disease protein. PolyQ expansion confers a dominant toxic property on the mutant protein that is associated with aberrant accumulation of the disease protein in neurons. All polyQ diseases are progressive, ultimately fatal disorders that typically begin in adulthood. Huntington disease (HD) is the best known polyQ disease, but at least seven hereditary ataxias and one motor neuron disease are also due to CAG repeat/polyQ expansion. Although the clinical features and patterns of neuronal degeneration differ among the diseases, increasing evidence suggests that polyQ diseases share important pathogenic features. In particular, expansion of the CAG repeat/polyQ domain confers upon the encoded protein a dominant toxic property. Thus as a therapeutic strategy, efforts to lower expression of the mutant gene product prior to cell death could be highly beneficial to patients.

Dominantly inherited diseases are ideal candidates for siRNA-based therapy. Expansions of poly-glutamine tracts in proteins that are expressed in the central nervous system can cause neurodegenerative diseases. Some neurodegenerative diseases are caused by a $(CAG)_n$ repeat that encodes polyglutamine in a protein include Huntington disease (HD), spinocerebellar ataxia (SCA1, SCA2, SCA3, SCA6, SCA7), spinal and bulbar muscular atrophy (SBMA), and dentatorubropallidoluysian atrophy (DRPLA). In these diseases, the poly-glutamine expansion in a protein confers a novel toxic property upon the protein. Studies indicate that the toxic property is a tendency for the disease protein to misfold and form aggregates within neurons. Clinical characteristics of HD include progressive loss of striatal neurons and later, cortical thinning. Adult patients show choreiform movements, impaired coordination, progressive dementia and other psychiatric disturbances. The symptoms of juvenile HD patients include bradykinesia, dystonia and seizures. HD is a uniformly fatal disease, with death occurring one to two decades after disease onset. In 38% of patients a polymorphism exists in exon 58 of the huntingtin gene, allowing for allele specific targeting.

The Hdh locus is on chromosome 4, spans 180 kb over 67 exons and encodes the protein huntingtin (htt). In non-HD individuals, the CAG repeat region is less than 35 CAG repeats. Expansions of 36 to ~50 repeats, or greater than ~50, cause late or early onset disease, respectively. The inverse correlation of repeat length with age of disease onset is a common characteristic of the CAG repeat disorders, and one that is recapitulated in mouse models. Evidence indicates that HD also may be a dose-dependent process. For example, in transgenic mouse models of polyQ disease, phenotypic severity usually correlates with expression levels of the disease protein, and homozygous transgenic mice develop disease more rapidly than heterozygous mice. In addition, the very rare human cases of homozygosity for polyQ disease suggest that disease severity correlates with the level of disease protein expression, again supporting the notion that reducing mutant protein expression would be clinically beneficial.

The function of htt is not known. It is clear from mouse models, however, that it is required during gastrulation, neurogenesis and in postnatal brain. Htt knock-out mice die during development. Also, removal of htt via Cre recombinase-mediated excision of a floxed Hdh allele causes progressive postnatal neurodegeneration. A CAG expansion introduced into the mouse allele (a knock-in) does not impair neurogenesis unless wildtype htt expression is reduced from normal levels, suggesting that the expanded allele does not impair wildtype htt function in neurogenesis. In adult mice mutant htt causes progressive depletion of normal htt. Htt is important in vesicle trafficking, NMDA receptor modulation, and regulation of BDNF transcription, and the expression of many genes is affected in the CNS of HD mice.

The therapeutic promise of silencing the mutant gene (and its toxic property) is best demonstrated in a tetracycline-regulated mouse model of HD. When mutant htt is inducibly expressed in these mice, pathological and behavioral features of the disease develop over time, including the characteristic formation of neuronal inclusions and abnormal motor behavior. However, when expression of the transgene is repressed in affected mice, the pathological and behavioral features of disease fully resolve. This result indicates that if expression of mutant polyQ protein can be halted, protein clearance mechanisms within neurons can eliminate the aggregated mutant protein, and possibly normalize mutant htt-induced changes. It also suggests that gene silencing approaches may be beneficial even for individuals with fairly advanced disease.

In the present invention, instead of targeting a SNP for allele specificity, the RNAi molecules take advantage of structural integrity at the sites flanking the expansion region.

To accomplish intracellular expression of the therapeutic RNAi molecules, an RNA molecule is constructed containing two complementary strands or a hairpin sequence (such as a 21-bp hairpin) representing sequences directed against the gene of interest. The RNAi molecule, or a nucleic acid encoding the RNAi molecule, is introduced to the target cell, such as a diseased brain cell. The RNAi molecule reduces target mRNA and protein expression.

The construct encoding the therapeutic RNAi molecule is configured such that the one or more strands of the RNAi molecules are encoded by a nucleic acid that is immediately contiguous to a promoter. In one example, the promoter is a pol II promoter. If a pol II promoter is used in a particular construct, it is selected from readily available pol II promoters known in the art, depending on whether regulatable, inducible, tissue or cell-specific expression of the siRNA is desired. The construct is introduced into the target cell, allowing for diminished target-gene expression in the cell.

The present invention provides an expression cassette containing an isolated nucleic acid sequence encoding an RNAi molecule targeted against a gene of interest. The RNAi molecule may form a hairpin structure that contains a duplex structure and a loop structure. The loop structure may contain from 4 to 10 nucleotides, such as 4, 5 or 6 nucleotides. The duplex is less than 30 nucleotides in length, such as from 19 to 25 nucleotides. The RNAi molecule may further contain an overhang region. Such an overhang may be a 3' overhang region or a 5' overhang region. The overhang region may be, for example, from 1 to 6 nucleotides in length. The expression cassette may further contain a pol II promoter, as described herein. Examples of pol II promoters include regulatable promoters and constitutive promoters. For example, the promoter may be a CMV or RSV promoter. The expression cassette may further contain a polyadenylation signal, such as a synthetic minimal polyadenylation signal. The nucleic acid sequence may further contain a marker gene or stuffer sequences. The expression cassette may be contained in a viral vector. An appropriate viral vector for use in the present invention may be an adenoviral, lentiviral, adeno-associated viral (AAV), poliovirus, herpes simplex virus (HSV) or murine Maloney-based viral vector. The gene of interest may be a gene associated with a condition amenable to siRNA therapy. Examples of such conditions include neurodegenerative diseases, such as a trinucleotide-repeat disease (e.g., polyglutamine repeat disease). Examples of these diseases include Huntington's disease or several spinocerebellar ataxias. Alternatively, the gene of interest may encode a ligand for a chemokine involved in the migration of a cancer cell, or a chemokine receptor.

The present invention also provides an expression cassette containing an isolated nucleic acid sequence encoding a first segment, a second segment located immediately 3' of the first segment, and a third segment located immediately 3' of the second segment, wherein the first and third segments are each less than 30 base pairs in length and each more than 10 base pairs in length, and wherein the sequence of the third segment is the complement of the sequence of the first segment, and wherein the isolated nucleic acid sequence functions as an RNAi molecule targeted against a gene of interest. The expression cassette may be contained in a vector, such as a viral vector.

The present invention provides a method of reducing the expression of a gene product in a cell by contacting a cell with an expression cassette described above. It also provides a method of treating a patient by administering to the patient a composition of the expression cassette described above.

The present invention further provides a method of reducing the expression of a gene product in a cell by contacting a cell with an expression cassette containing an isolated nucleic acid sequence encoding a first segment, a second segment located immediately 3' of the first segment, and a third segment located immediately 3' of the second segment, wherein the first and third segments are each less than 30 base pairs in length and each more than 10 base pairs in length, and wherein the sequence of the third segment is the complement of the sequence of the first segment, and wherein the isolated nucleic acid sequence functions as an RNAi molecule targeted against a gene of interest.

The present method also provides a method of treating a patient, by administering to the patient a composition containing an expression cassette, wherein the expression cassette contains an isolated nucleic acid sequence encoding a first segment, a second segment located immediately 3' of the first segment, and a third segment located immediately 3' of the second segment, wherein the first and third segments are each less than 30 bases in length and each more than 10 bases in length, and wherein the sequence of the third segment is the complement of the sequence of the first segment, and wherein the isolated nucleic acid sequence functions as an RNAi molecule targeted against a gene of interest.

I. RNA Interference (RNAi) Molecule

An RNAi molecule may be a "small interfering RNA" or "short interfering RNA" or "siRNA" or "short hairpin RNA" or "shRNA" or "microRNA" or "miRNA." An RNAi molecule an RNA duplex of nucleotides that is targeted to a nucleic acid sequence of interest, for example, ataxin-1 or huntingtin (htt). As used herein, the term "RNAi molecule" is a generic term that encompasses the subset of shRNAs. A "RNA duplex" refers to the structure formed by the complementary pairing between two regions of a RNA molecule. RNAi molecule is "targeted" to a gene in that the nucleotide sequence of the duplex portion of the RNAi molecule is complementary to a nucleotide sequence of the targeted gene. In certain embodiments, the RNAi molecules are targeted to the sequence encoding huntingtin. In some embodiments, the length of the duplex of RNAi molecules is less than 30 base pairs. In some embodiments, the duplex can be 29, 28, 27, 26, 25, 24, 23, 22, 21, 20, 19, 18, 17, 16, 15, 14, 13, 12, 11 or 10 base pairs in length. In some embodiments, the length of the duplex is 19 to 25 base pairs in length. In certain embodiment, the length of the duplex is 19 or 21 base pairs in length. The RNA duplex portion of the RNAi molecule can be part of a hairpin structure. In addition to the duplex portion, the hairpin structure may contain a loop portion positioned between the two sequences that form the duplex. The loop can vary in length. In some embodiments the loop is 5, 6, 7, 8, 9, 10, 11, 12 or 13 nucleotides in length. In certain embodiments, the loop is 9 nucleotides in length. The hairpin structure can also contain 3' or 5' overhang portions. In some embodiments, the overhang is a 3' or a 5' overhang 0, 1, 2, 3, 4 or 5 nucleotides in length.

The RNAi molecule can be encoded by a nucleic acid sequence, and the nucleic acid sequence can also include a promoter. The nucleic acid sequence can also include a polyadenylation signal. In some embodiments, the polyadenylation signal is a synthetic minimal polyadenylation signal.

"Knock-down," "knock-down technology" refers to a technique of gene silencing in which the expression of a target gene is reduced as compared to the gene expression prior to the introduction of the RNAi molecule, which can lead to the inhibition of production of the target gene product. The term "reduced" is used herein to indicate that the target gene expression is lowered by 1-100%. In other words, the amount of RNA available for translation into a polypeptide or protein is minimized. For example, the amount of protein may be reduced by 10, 20, 30, 40, 50, 60, 70, 80, 90, 95, or 99%. In some embodiments, the expression is reduced by about 90% (i.e., only about 10% of the amount of protein is observed a cell as compared to a cell where RNAi molecules have not been administered). Knock-down of gene expression can be directed, for example, by the use of dsRNAs, siRNAs or miRNAs.

"RNA interference (RNAi)" is the process of sequence-specific, post-transcriptional gene silencing initiated by an RNAi molecule. During RNAi, RNAi molecules induce degradation of target mRNA with consequent sequence-specific inhibition of gene expression. RNAi involving the use of RNAi molecules has been successfully applied to knockdown the expression of specific genes in plants, *D. melanogaster, C. elegans*, trypanosomes, planaria, hydra, and several vertebrate species including the mouse.

According to a method of the present invention, the expression of huntingtin can be modified via RNAi. For example, the accumulation of huntingtin can be suppressed in a cell. The term "suppressing" refers to the diminution, reduction or elimination in the number or amount of transcripts present in a particular cell. For example, the accumulation of mRNA encoding huntingtin can be suppressed in a cell by RNA interference (RNAi), e.g., the gene is silenced by sequence-specific double-stranded RNA (dsRNA), which is also called short interfering RNA (siRNA). These siRNAs can be two separate RNA molecules that have hybridized together, or they may be a single hairpin wherein two portions of a RNA molecule have hybridized together to form a duplex.

A mutant protein refers to the protein encoded by a gene having a mutation, e.g., a missense or nonsense mutation in one or both alleles of huntingtin. A mutant huntingtin may be disease-causing, i.e., may lead to a disease associated with the presence of huntingtin in an animal having either one or two mutant allele(s).

The term "gene" is used broadly to refer to any segment of nucleic acid associated with a biological function. Thus, genes include coding sequences and/or the regulatory sequences required for their expression. For example, "gene" refers to a nucleic acid fragment that expresses mRNA, functional RNA, or specific protein, including regulatory sequences. "Genes" also include nonexpressed DNA segments that, for example, form recognition sequences for other proteins. "Genes" can be obtained from a variety of sources, including cloning from a source of interest or synthesizing from known or predicted sequence information, and may include sequences designed to have desired parameters. An "allele" is one of several alternative forms of a gene occupying a given locus on a chromosome.

The term "nucleic acid" refers to deoxyribonucleic acid (DNA) or ribonucleic acid (RNA) and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues. A "nucleic acid fragment" is a portion of a given nucleic acid molecule.

A "nucleotide sequence" is a polymer of DNA or RNA that can be single- or double-stranded, optionally containing synthetic, non-natural or altered nucleotide bases capable of incorporation into DNA or RNA polymers.

The terms "nucleic acid," "nucleic acid molecule," "nucleic acid fragment," "nucleic acid sequence or segment," or "polynucleotide" are used interchangeably and may also be used interchangeably with gene, cDNA, DNA and RNA encoded by a gene.

The invention encompasses isolated or substantially purified nucleic acid compositions. In the context of the present invention, an "isolated" or "purified" DNA molecule or RNA molecule is a DNA molecule or RNA molecule that exists apart from its native environment and is therefore not a product of nature. An isolated DNA molecule or RNA molecule may exist in a purified form or may exist in a non-native environment such as, for example, a transgenic host cell. For example, an "isolated" or "purified" nucleic acid molecule or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. Fragments and variants of the disclosed nucleotide sequences are also encompassed by the present invention. By "fragment" or "portion" is meant a full length or less than full length of the nucleotide sequence.

"Naturally occurring," "native," or "wild-type" is used to describe an object that can be found in nature as distinct from being artificially produced. For example, a protein or nucleotide sequence present in an organism (including a virus), which can be isolated from a source in nature and that has not been intentionally modified by a person in the laboratory, is naturally occurring.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of molecular biology techniques, as, for example, with polymerase chain reaction (PCR) and hybridization techniques. Variant nucleotide sequences also include synthetically derived nucleotide sequences, such as those generated, for example, by using site-directed mutagenesis, which encode the native protein, as well as those that encode a polypeptide having amino acid substitutions. Generally, nucleotide sequence variants of the invention will have at least 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

The term "chimeric" refers to a gene or DNA that contains 1) DNA sequences, including regulatory and coding sequences that are not found together in nature or 2) sequences encoding parts of proteins not naturally adjoined, or 3) parts of promoters that are not naturally adjoined. Accordingly, a chimeric gene may include regulatory sequences and coding sequences that are derived from different sources, or include regulatory sequences and coding sequences derived from the same source, but arranged in a manner different from that found in nature.

A "transgene" refers to a gene that has been introduced into the genome by transformation. Transgenes include, for example, DNA that is either heterologous or homologous to the DNA of a particular cell to be transformed. Additionally, transgenes may include native genes inserted into a non-native organism, or chimeric genes.

The term "endogenous gene" refers to a native gene in its natural location in the genome of an organism.

A "foreign" gene refers to a gene not normally found in the host organism that has been introduced by gene transfer.

The terms "protein," "peptide" and "polypeptide" are used interchangeably herein.

"Conservatively modified variations" of a particular nucleic acid sequence refers to those nucleic acid sequences that encode identical or essentially identical amino acid sequences. Because of the degeneracy of the genetic code, a large number of functionally identical nucleic acids encode any given polypeptide. For instance, the codons CGT, CGC, CGA, CGG, AGA and AGG all encode the amino acid arginine. Thus, at every position where an arginine is specified by a codon, the codon can be altered to any of the corresponding codons described without altering the encoded protein. Such nucleic acid variations are "silent variations," which are one species of "conservatively modified variations." Every nucleic acid sequence described herein that encodes a polypeptide also describes every possible silent variation, except where otherwise noted. One of skill in the art will recognize that each codon in a nucleic acid (except ATG, which is ordinarily the only codon for methionine) can be modified to yield a functionally identical molecule by standard techniques. Accordingly, each "silent variation" of a nucleic acid that encodes a polypeptide is implicit in each described sequence.

"Recombinant DNA molecule" is a combination of DNA sequences that are joined together using recombinant DNA technology and procedures used to join together DNA sequences as described, for example, in Sambrook and Russell (2001).

The terms "heterologous gene," "heterologous DNA sequence," "exogenous DNA sequence," "heterologous RNA sequence," "exogenous RNA sequence" or "heterologous nucleic acid" each refer to a sequence that either originates from a source foreign to the particular host cell, or is from the same source but is modified from its original or native form. Thus, a heterologous gene in a host cell includes a gene that is endogenous to the particular host cell but has been modified through, for example, the use of DNA shuffling. The terms also include non-naturally occurring multiple copies of a naturally occurring DNA or RNA sequence. Thus, the terms refer to a DNA or RNA segment that is foreign or heterologous to the cell, or homologous to the cell but in a position within the host cell nucleic acid in which the element is not ordinarily found. Exogenous DNA segments are expressed to yield exogenous polypeptides.

A "homologous" DNA or RNA sequence is a sequence that is naturally associated with a host cell into which it is introduced.

"Wild-type" refers to the normal gene or organism found in nature.

"Genome" refers to the complete genetic material of an organism.

A "vector" is defined to include, inter alia, any viral vector, as well as any plasmid, cosmid, phage or binary vector in double or single stranded linear or circular form that may or may not be self transmissible or mobilizable, and that can transform prokaryotic or eukaryotic host either by integration into the cellular genome or exist extrachromosomally (e.g., autonomous replicating plasmid with an origin of replication).

"Expression cassette" as used herein means a nucleic acid sequence capable of directing expression of a particular nucleotide sequence in an appropriate host cell, which may include a promoter operably linked to the nucleotide sequence of interest that may be operably linked to termination signals. The coding region usually codes for a functional RNA of interest, for example an RNAi molecule. The expression cassette including the nucleotide sequence of interest may be chimeric. The expression cassette may also be one that is naturally occurring but has been obtained in a recombinant form useful for heterologous expression. The expression of the nucleotide sequence in the expression cassette may be under the control of a constitutive promoter or of a regulatable promoter that initiates transcription only when the host cell is exposed to some particular stimulus. In the case of a multicellular organism, the promoter can also be specific to a particular tissue or organ or stage of development.

Such expression cassettes can include a transcriptional initiation region linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

"Coding sequence" refers to a DNA or RNA sequence that codes for a specific amino acid sequence. It may constitute an "uninterrupted coding sequence", i.e., lacking an intron, such as in a cDNA, or it may include one or more introns bounded by appropriate splice junctions. An "intron" is a sequence of RNA that is contained in the primary transcript but is removed through cleavage and re-ligation of the RNA within the cell to create the mature mRNA that can be translated into a protein.

The term "open reading frame" (ORF) refers to the sequence between translation initiation and termination codons of a coding sequence. The terms "initiation codon" and "termination codon" refer to a unit of three adjacent nucleotides (a 'codon') in a coding sequence that specifies initiation and chain termination, respectively, of protein synthesis (mRNA translation).

"Functional RNA" refers to sense RNA, antisense RNA, ribozyme RNA, siRNA, or other RNA that may not be translated but yet has an effect on at least one cellular process.

The term "RNA transcript" or "transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA.

"Regulatory sequences" are nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences that may be a combination of synthetic and natural sequences. As is noted above, the term "suitable regulatory sequences" is not limited to promoters. However, some suitable regulatory sequences useful in the present invention will include, but are not limited to constitutive promoters, tissue-specific promoters, development-specific promoters, regulatable promoters and viral promoters.

"5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency.

"3' non-coding sequence" refers to nucleotide sequences located 3' (downstream) to a coding sequence and may include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor.

The term "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

The term "mature" protein refers to a post-translationally processed polypeptide without its signal peptide. "Precursor" protein refers to the primary product of translation of an mRNA. "Signal peptide" refers to the amino terminal extension of a polypeptide, which is translated in conjunction with the polypeptide forming a precursor peptide and which is required for its entrance into the secretory pathway. The term "signal sequence" refers to a nucleotide sequence that encodes the signal peptide.

"Promoter" refers to a nucleotide sequence, usually upstream (5') to its coding sequence, which directs and/or controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions. Examples of promoters that may be used in the present invention include the mouse U6 RNA promoters, synthetic human H1RNA promoters, SV40, CMV, RSV, RNA polymerase II and RNA polymerase III promoters.

The "initiation site" is the position surrounding the first nucleotide that is part of the transcribed sequence, which is also defined as position +1. With respect to this site all other sequences of the gene and its controlling regions are numbered. Downstream sequences (i.e., further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

"Constitutive expression" refers to expression using a constitutive or regulated promoter. "Conditional" and "regulated expression" refer to expression controlled by a regulated promoter.

"Operably-linked" refers to the association of nucleic acid sequences on single nucleic acid fragment so that the function of one of the sequences is affected by another. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation of an endogenous gene, heterologous gene or nucleic acid segment, or a transgene in cells. For example, in the case of siRNA constructs, expression may refer to the transcription of the siRNA only. In addition, expression refers to the transcription and stable accumulation of sense (mRNA) or functional RNA. Expression may also refer to the production of protein.

"Altered levels" refers to the level of expression in transgenic cells or organisms that differs from that of normal or untransformed cells or organisms.

"Overexpression" refers to the level of expression in transgenic cells or organisms that exceeds levels of expression in normal or untransformed cells or organisms.

"Antisense inhibition" refers to the production of antisense RNA transcripts capable of suppressing the expression of protein from an endogenous gene or a transgene.

"Transcription stop fragment" refers to nucleotide sequences that contain one or more regulatory signals, such as polyadenylation signal sequences, capable of terminating transcription. Examples include the 3' non-regulatory regions of genes encoding nopaline synthase and the small subunit of ribulose bisphosphate carboxylase.

"Translation stop fragment" refers to nucleotide sequences that contain one or more regulatory signals, such as one or more termination codons in all three frames, capable of terminating translation. Insertion of a translation stop fragment adjacent to or near the initiation codon at the 5' end of the coding sequence will result in no translation or improper translation. Excision of the translation stop fragment by site-specific recombination will leave a site-specific sequence in the coding sequence that does not interfere with proper translation using the initiation codon.

The terms "cis-acting sequence" and "cis-acting element" refer to DNA or RNA sequences whose functions require them to be on the same molecule. An example of a cis-acting sequence on the replicon is the viral replication origin.

The terms "trans-acting sequence" and "trans-acting element" refer to DNA or RNA sequences whose function does not require them to be on the same molecule.

"Chromosomally-integrated" refers to the integration of a foreign gene or nucleic acid construct into the host DNA by covalent bonds. Where genes are not "chromosomally integrated" they may be "transiently expressed." Transient expression of a gene refers to the expression of a gene that is not integrated into the host chromosome but functions independently, either as part of an autonomously replicating plasmid or expression cassette, for example, or as part of another biological system such as a virus.

The following terms are used to describe the sequence relationships between two or more nucleic acids or polynucleotides: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well-known in the art. Thus, the determination of percent identity between any two sequences can be accomplished using a mathematical algorithm.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues;

always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized. Alternatively, PSI-BLAST (in BLAST 2.0) can be used to perform an iterated search that detects distant relationships between molecules. When utilizing BLAST, Gapped BLAST, PSI-BLAST, the default parameters of the respective programs (e.g. BLASTN for nucleotide sequences) can be used. The BLASTN program (for nucleotide sequences) uses as defaults a wordlength (W) of 11, an expectation (E) of 10, a cutoff of 100, M=5, N=−4, and a comparison of both strands. Alignment may also be performed manually by inspection.

For purposes of the present invention, comparison of nucleotide sequences for determination of percent sequence identity to the promoter sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide matches and an identical percent sequence identity when compared to the corresponding alignment generated by the preferred program.

(c) As used herein, "sequence identity" or "identity" in the context of two nucleic acid sequences makes reference to a specified percentage of nucleotides in the two sequences that are the same when aligned for maximum correspondence over a specified comparison window, as measured by sequence comparison algorithms or by visual inspection.

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e) The term "substantial identity" of polynucleotide sequences means that a polynucleotide comprises a sequence that has at least 70%, 71%, 72%, 73%, 74%, 75%, 76%, 77%, 78%, or 79%, preferably at least 80%, 81%, 82%, 83%, 84%, 85%, 86%, 87%, 88%, or 89%, more preferably at least 90%, 91%, 92%, 93%, or 94%, and most preferably at least 95%, 96%, 97%, 98%, or 99% sequence identity, compared to a reference sequence using one of the alignment programs described using standard parameters.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The $T_m$ is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl:

$$T_m 81.5° C. + 16.6(\log M) + 0.41(\% GC) - 0.61(\% \text{form}) - 500/L;$$

where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. Generally, highly stringent hybridization and wash conditions are selected to be about 5° C. lower than the $T_m$ for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see, Sambrook and Russell 2001, for a description of SSC buffer). Often, a high stringency wash is preceded by a low stringency wash to remove background probe signal. For short nucleic acid sequences (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. Stringent conditions may also be achieved with the addition of destabilizing agents such as formamide. In general, a signal to noise ratio of 2× (or higher) than that observed for an unrelated probe in the particular hybridization assay indicates detection of a specific hybridization. Very stringent conditions are selected to be equal to the Tm for a particular nucleic acid molecule.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

The term "transformation" refers to the transfer of a nucleic acid fragment into the genome of a host cell, resulting in genetically stable inheritance. A "host cell" is a cell that has been transformed, or is capable of transformation, by an exogenous nucleic acid molecule. Host cells containing the transformed nucleic acid fragments are referred to as "transgenic" cells.

"Transformed," "transduced," "transgenic" and "recombinant" refer to a host cell into which a heterologous nucleic acid molecule has been introduced. As used herein the term "transfection" refers to the delivery of DNA into eukaryotic (e.g., mammalian) cells. The term "transformation" is used herein to refer to delivery of DNA into prokaryotic (e.g., E. coli) cells. The term "transduction" is used herein to refer to infecting cells with viral particles. The nucleic acid molecule can be stably integrated into the genome generally known in the art. Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" cells have been through the transformation process and contain a foreign gene integrated into their chromosome. The term "untransformed" refers to normal cells that have not been through the transformation process.

"Genetically altered cells" denotes cells which have been modified by the introduction of recombinant or heterologous nucleic acids (e.g., one or more DNA constructs or their RNA counterparts) and further includes the progeny of such cells which retain part or all of such genetic modification.

As used herein, the term "derived" or "directed to" with respect to a nucleotide molecule means that the molecule has complementary sequence identity to a particular molecule of interest.

"Gene silencing" refers to the suppression of gene expression, e.g., transgene, heterologous gene and/or endogenous gene expression. Gene silencing may be mediated through processes that affect transcription and/or through processes that affect post-transcriptional mechanisms. In some embodiments, gene silencing occurs when siRNA initiates the degradation of the mRNA of a gene of interest in a sequence-specific manner via RNA interference. In some embodiments, gene silencing may be allele-specific. "Allele-specific" gene silencing refers to the specific silencing of one allele of a gene.

"Knock-down," "knock-down technology" refers to a technique of gene silencing in which the expression of a target gene is reduced as compared to the gene expression prior to the introduction of the RNAi molecule, which can lead to the inhibition of production of the target gene product. The term "reduced" is used herein to indicate that the target gene expression is lowered by 1-100%. For example, the expression may be reduced by 10, 20, 30, 40, 50, 60, 70, 80, 90, 95, or even 99%. Knock-down of gene expression can be directed by the use of dsRNAs or siRNAs. For example, "RNA interference (RNAi)," which can involve the use of siRNA, has been successfully applied to knockdown the expression of specific genes in plants, D. melanogaster, C. elegans, trypanosomes, planaria, hydra, and several vertebrate species including the mouse.

"RNA interference (RNAi)" is the process of sequence-specific, post-transcriptional gene silencing initiated by siRNA. RNAi is seen in a number of organisms such as Drosophila, nematodes, fungi and plants, and is believed to be involved in anti-viral defense, modulation of transposon activity, and regulation of gene expression. During RNAi, RNAi molecules induce degradation of target mRNA with consequent sequence-specific inhibition of gene expression.

A "small interfering" or "short interfering RNA" or siRNA is a RNA duplex of nucleotides that is targeted to a gene interest. A "RNA duplex" refers to the structure formed by the complementary pairing between two regions of a RNA molecule. siRNA is "targeted" to a gene in that the nucleotide sequence of the duplex portion of the siRNA is complementary to a nucleotide sequence of the targeted gene. In some embodiments, the length of the duplex of siRNAs is less than 30 nucleotides. In some embodiments, the duplex can be 29, 28, 27, 26, 25, 24, 23, 22, 21, 20, 19, 18, 17, 16, 15, 14, 13, 12, 11 or 10 nucleotides in length. In some embodiments, the length of the duplex is 19-25 nucleotides in length. The RNA duplex portion of the siRNA can be part of a hairpin structure. In addition to the duplex portion, the hairpin structure may contain a loop portion positioned between the two sequences that form the duplex. The loop can vary in length. In some embodiments the loop is 5, 6, 7, 8, 9, 10, 11, 12 or 13 nucleotides in length. The hairpin structure can also contain 3' or 5' overhang portions. In some embodiments, the overhang is a 3' or a 5' overhang 0, 1, 2, 3, 4 or 5 nucleotides in length. The "sense" and "antisense" sequences can be used with or without a loop region to form siRNA molecules. As used herein, the term siRNA is meant to be equivalent to other terms used to describe nucleic acid molecules that are capable of mediating sequence specific RNAi, for example, double-stranded RNA (dsRNA), micro-RNA (miRNA), short hairpin RNA (shRNA), short interfering oligonucleotide, short interfering nucleic acid, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetic silencing. For example, siRNA molecules of the invention can be used to epigenetically silence genes at both the post-transcriptional level or the pre-transcriptional level. In a non-limiting example, epigenetic modulation of gene expression by siRNA molecules of the invention can result from siRNA mediated modification of chromatin structure or methylation pattern to alter gene expression. In another non-limiting example, modulation of gene expression by siRNA molecules of the invention can result from siRNA mediated cleavage of RNA (either coding or non-coding RNA) via RISC, or alternately, translational inhibition as is known in the art.

The siRNA can be encoded by a nucleic acid sequence, and the nucleic acid sequence can also include a promoter. The nucleic acid sequence can also include a polyadenylation signal. In some embodiments, the polyadenylation signal is a synthetic minimal polyadenylation signal.

"Treating" as used herein refers to ameliorating at least one symptom of, curing and/or preventing the development of a disease or a condition.

"Neurological disease" and "neurological disorder" refer to both hereditary and sporadic conditions that are characterized by nervous system dysfunction, and which may be associated with atrophy of the affected central or peripheral nervous system structures, or loss of function without atrophy. A neurological disease or disorder that results in atrophy is commonly called a "neurodegenerative disease" or "neurodegenerative disorder." Neurodegenerative diseases and disorders include, but are not limited to, amyotrophic lateral sclerosis (ALS), hereditary spastic hemiplegia, primary lateral sclerosis, spinal muscular atrophy, Kennedy's disease, Alzheimer's disease, Parkinson's disease, multiple sclerosis, and repeat expansion neurodegenerative diseases, e.g., diseases associated with expansions of trinucleotide repeats such as polyglutamine (polyQ) repeat diseases, e.g., Huntington's disease (HD), spinocerebellar ataxia (SCA1, SCA2, SCA3, SCA6, SCA7, and SCA17), spinal and bulbar muscular atrophy (SBMA), dentatorubropallidoluysian atrophy (DRPLA). An example of a neurological disorder that does not appear to result in atrophy is DYT1 dystonia.

The RNAi molecules of the present invention can be generated by any method known to the art, for example, by in vitro transcription, recombinantly, or by synthetic means. In one example, the RNAi molecules can be generated in vitro by using a recombinant enzyme, such as T7 RNA polymerase, and DNA oligonucleotide templates.

II. Nucleic Acid Molecules of the Invention

The terms "isolated and/or purified" refer to in vitro isolation of a nucleic acid, e.g., a DNA or RNA molecule from its natural cellular environment, and from association with other components of the cell, such as nucleic acid or polypeptide, so that it can be sequenced, replicated, and/or expressed. For example, "isolated nucleic acid" may be a DNA molecule containing less than 31 sequential nucleotides that is transcribed into an RNAi molecule. Such an isolated RNAi molecule may, for example, form a hairpin structure with a duplex 21 base pairs in length that is complementary or hybridizes to a sequence in a gene of interest, and remains stably bound under stringent conditions (as defined by methods well known in the art, e.g., in Sambrook and Russell, 2001). Thus, the RNA or DNA is "isolated" in that it is free from at least one contaminating nucleic acid with which it is normally associated in the natural source of the RNA or DNA and is preferably substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell, e.g., in a vector or plasmid.

In addition to a DNA sequence encoding a siRNA, the nucleic acid molecules of the invention include double-stranded interfering RNA molecules, which are also useful to inhibit expression of a target gene.

As used herein, the term "recombinant nucleic acid", e.g., "recombinant DNA sequence or segment" refers to a nucleic acid, e.g., to DNA, that has been derived or isolated from any appropriate cellular source, that may be subsequently chemically altered in vitro, so that its sequence is not naturally occurring, or corresponds to naturally occurring sequences that are not positioned as they would be positioned in a genome which has not been transformed with exogenous DNA. An example of preselected DNA "derived" from a source would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Thus, recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. Therefore, "recombinant DNA" includes completely synthetic DNA sequences, semi-synthetic DNA sequences, DNA sequences isolated from biological sources, and DNA sequences derived from RNA, as well as mixtures thereof.

Nucleic acid molecules having base substitutions (i.e., variants) are prepared by a variety of methods known in the art. These methods include, but are not limited to, isolation from a natural source (in the case of naturally occurring sequence variants) or preparation by oligonucleotide-mediated (or site-directed) mutagenesis, PCR mutagenesis, and cassette mutagenesis of an earlier prepared variant or a non-variant version of the nucleic acid molecule.

Oligonucleotide-mediated mutagenesis is a method for preparing substitution variants. Briefly, nucleic acid encoding a siRNA can be altered by hybridizing an oligonucleotide encoding the desired mutation to a DNA template, where the template is the single-stranded form of a plasmid or bacteriophage containing the unaltered or native gene sequence. After hybridization, a DNA polymerase is used to synthesize an entire second complementary strand of the template that will thus incorporate the oligonucleotide primer, and will code for the selected alteration in the nucleic acid encoding siRNA. Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art.

The DNA template can be generated by those vectors that are either derived from bacteriophage M13 vectors (the commercially available M13mp18 and M13mp19 vectors are suitable), or those vectors that contain a single-stranded phage origin of replication. Thus, the DNA that is to be mutated may be inserted into one of these vectors to generate single-stranded template. Production of the single-stranded template is described in Chapter 3 of Sambrook and Russell, 2001. Alternatively, single-stranded DNA template may be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of the DNA, and the other strand (the original template) encodes the native, unaltered sequence of the DNA. This heteroduplex molecule is then transformed into a suitable host cell, usually a prokaryote such as E. coli JM101. After the cells are grown, they are plated onto agarose plates and screened using the oligonucleotide primer radiolabeled with 32-phosphate to identify the bacterial colonies that contain the mutated DNA. The mutated region is then removed and placed in an appropriate vector, generally an expression vector of the type typically employed for transformation of an appropriate host.

The method described immediately above may be modified such that a homoduplex molecule is created wherein both strands of the plasmid contain the mutations(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thiodeoxyribocytosine called dCTP-(*S) (which can be obtained from the Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-(*S) instead of dCTP, which serves to protect it from restriction endonuclease digestion.

After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as E. coli JM101.

There are well-established criteria for designing siRNAs. However, since the mechanism for siRNAs suppressing gene expression is not entirely understood and siRNAs selected from different regions of the same gene do not work as equally effective, very often a number of siRNAs have to be generated at the same time in order to compare their effectiveness.

III. Expression Cassettes of the Invention

To prepare expression cassettes, the recombinant DNA sequence or segment may be circular or linear, double-stranded or single-stranded. Generally, the DNA sequence or segment is in the form of chimeric DNA, such as plasmid DNA or a vector that can also contain coding regions flanked by control sequences that promote the expression of the recombinant DNA present in the resultant transformed cell.

A "chimeric" vector or expression cassette, as used herein, means a vector or cassette including nucleic acid sequences from at least two different species, or has a nucleic acid sequence from the same species that is linked or associated in a manner that does not occur in the "native" or wild type of the species.

Aside from recombinant DNA sequences that serve as transcription units for an RNA transcript, or portions thereof, a portion of the recombinant DNA may be untranscribed, serving a regulatory or a structural function. For example, the recombinant DNA may have a promoter that is active in mammalian cells.

Other elements functional in the host cells, such as introns, enhancers, polyadenylation sequences and the like, may also be a part of the recombinant DNA. Such elements may or may not be necessary for the function of the DNA, but may provide improved expression of the DNA by affecting transcription, stability of the siRNA, or the like. Such elements may be included in the DNA as desired to obtain the optimal performance of the siRNA in the cell.

Control sequences are DNA sequences necessary for the expression of an operably linked coding sequence in a particular host organism. The control sequences that are suitable for prokaryotic cells, for example, include a promoter, and optionally an operator sequence, and a ribosome binding site. Eukaryotic cells are known to utilize promoters, polyadenylation signals, and enhancers.

Operably linked nucleic acids are nucleic acids placed in a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation. Generally, operably linked DNA sequences are DNA sequences that are linked are contiguous. However, enhancers do not have to be contiguous. Linking is accomplished by ligation at convenient restriction sites. If such sites do not exist, the synthetic oligonucleotide adaptors or linkers are used in accord with conventional practice.

The recombinant DNA to be introduced into the cells may contain either a selectable marker gene or a reporter gene or both to facilitate identification and selection of expressing cells from the population of cells sought to be transfected or infected through viral vectors. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neo and the like.

Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. For example, reporter genes include the chloramphenicol acetyl transferase gene (cat) from Tn9 of *E. coli* and the luciferase gene from firefly *Photinus pyralis*. Expression of the reporter gene is assayed at a suitable time after the DNA has been introduced into the recipient cells.

The general methods for constructing recombinant DNA that can transfect target cells are well known to those skilled in the art, and the same compositions and methods of construction may be utilized to produce the DNA useful herein.

The recombinant DNA can be readily introduced into the host cells, e.g., mammalian, bacterial, yeast or insect cells by transfection with an expression vector composed of DNA encoding the siRNA by any procedure useful for the introduction into a particular cell, e.g., physical or biological methods, to yield a cell having the recombinant DNA stably integrated into its genome or existing as a episomal element, so that the DNA molecules, or sequences of the present invention are expressed by the host cell. Preferably, the DNA is introduced into host cells via a vector. The host cell is preferably of eukaryotic origin, e.g., plant, mammalian, insect, yeast or fungal sources, but host cells of non-eukaryotic origin may also be employed.

Physical methods to introduce a preselected DNA into a host cell include calcium phosphate precipitation, lipofection, particle bombardment, microinjection, electroporation, and the like. Biological methods to introduce the DNA of interest into a host cell include the use of DNA and RNA viral vectors. For mammalian gene therapy, as described herein below, it is desirable to use an efficient means of inserting a copy gene into the host genome. Viral vectors, and especially retroviral vectors, have become the most widely used method for inserting genes into mammalian, e.g., human cells. Other viral vectors can be derived from poxviruses, herpes simplex virus I, adenoviruses and adeno-associated viruses, and the like.

As discussed above, a "transfected" or "transduced" host cell or cell line is one in which the genome has been altered or augmented by the presence of at least one heterologous or recombinant nucleic acid sequence. The host cells of the present invention are typically produced by transfection with a DNA sequence in a plasmid expression vector, a viral expression vector, or as an isolated linear DNA sequence. The transfected DNA can become a chromosomally integrated recombinant DNA sequence, which is composed of sequence encoding the siRNA.

To confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

To detect and quantitate RNA produced from introduced recombinant DNA segments, RT-PCR may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the recombinant DNA segment in question, they do not provide information as to whether the preselected DNA segment is being expressed. Expression may be evaluated by specifically identifying the peptide products of the introduced recombinant DNA sequences or evaluating the phenotypic changes brought about by the expression of the introduced recombinant DNA segment in the host cell.

The instant invention provides a cell expression system for expressing exogenous nucleic acid material in a mammalian recipient. The expression system, also referred to as a "genetically modified cell," comprises a cell and an expression vector for expressing the exogenous nucleic acid material. The genetically modified cells are suitable for administration to a mammalian recipient, where they replace the endogenous cells of the recipient. Thus, the preferred genetically modified cells are non-immortalized and are non-tumorigenic.

According to one embodiment, the cells are transfected or otherwise genetically modified ex vivo. The cells are isolated from a mammal (preferably a human), nucleic acid introduced (i.e., transduced or transfected in vitro) with a vector for expressing a heterologous (e.g., recombinant) gene encoding the therapeutic agent, and then administered to a mammalian recipient for delivery of the therapeutic agent in situ. The mammalian recipient may be a human and the cells to be modified are autologous cells, i.e., the cells are isolated from the mammalian recipient.

According to another embodiment, the cells are transfected or transduced or otherwise genetically modified in vivo. The cells from the mammalian recipient are transduced or transfected in vivo with a vector containing exogenous nucleic acid material for expressing a heterologous (e.g., recombinant) gene encoding a therapeutic agent and the therapeutic agent is delivered in situ.

As used herein, "exogenous nucleic acid material" refers to a nucleic acid or an oligonucleotide, either natural or synthetic, which is not naturally found in the cells; or if it is naturally found in the cells, is modified from its original or native form. Thus, "exogenous nucleic acid material" includes, for example, a non-naturally occurring nucleic acid that can be transcribed into an anti-sense RNA, a siRNA, as well as a "heterologous gene" (i.e., a gene encoding a protein that is not expressed or is expressed at biologically insignificant levels in a naturally-occurring cell of the same type). To illustrate, a synthetic or natural gene encoding human erythropoietin (EPO) would be considered "exogenous nucleic acid material" with respect to human peritoneal mesothelial cells since the latter cells do not naturally express EPO. Still another example of "exogenous nucleic acid material" is the introduction of only part of a gene to create a recombinant gene, such as combining an regulatable promoter with an endogenous coding sequence via homologous recombination.

IV. MicroRNA Shuttles for RNAi miRNAs are small cellular RNAs (~22 nt) that are processed from precursor stem loop transcripts. Known miRNA stem loops can be modified to contain RNAi sequences specific for genes of interest. miRNA molecules can be preferable over shRNA molecules because miRNAs are endogenously expressed. Therefore, miRNA molecules are unlikely to induce dsRNA-responsive interferon pathways, they are processed more efficiently than shRNAs, and they have been shown to silence 80% more effectively.

Also, the promoter roles are different for miRNA molecules as compared to shRNA molecules. Tissue-specific, inducible expression of shRNAs involves truncation of polII promoters to the transcription start site. In contrast, miRNAs can be expressed from any polII promoter because the transcription start and stop sites can be relatively arbitrary.

V. Methods for Introducing the Expression Cassettes of the Invention into Cells

The condition amenable to gene inhibition therapy may be a prophylactic process, i.e., a process for preventing disease or an undesired medical condition. Thus, the instant invention embraces a system for delivering siRNA that has a prophylactic function (i.e., a prophylactic agent) to the mammalian recipient.

The inhibitory nucleic acid material (e.g., an expression cassette encoding siRNA directed to a gene of interest) can be introduced into the cell ex vivo or in vivo by genetic transfer methods, such as transfection or transduction, to provide a genetically modified cell. Various expression vectors (i.e., vehicles for facilitating delivery of exogenous nucleic acid into a target cell) are known to one of ordinary skill in the art.

As used herein, "transfection of cells" refers to the acquisition by a cell of new nucleic acid material by incorporation of added DNA. Thus, transfection refers to the insertion of nucleic acid into a cell using physical or chemical methods. Several transfection techniques are known to those of ordinary skill in the art including calcium phosphate DNA co-precipitation, DEAE-dextran, electroporation, cationic liposome-mediated transfection, tungsten particle-facilitated microparticle bombardment, and strontium phosphate DNA co-precipitation.

In contrast, "transduction of cells" refers to the process of transferring nucleic acid into a cell using a DNA or RNA virus. A RNA virus (i.e., a retrovirus) for transferring a nucleic acid into a cell is referred to herein as a transducing chimeric retrovirus. Exogenous nucleic acid material contained within the retrovirus is incorporated into the genome of the transduced cell. A cell that has been transduced with a chimeric DNA virus (e.g., an adenovirus carrying a cDNA encoding a therapeutic agent), will not have the exogenous nucleic acid material incorporated into its genome but will be capable of expressing the exogenous nucleic acid material that is retained extrachromosomally within the cell.

The exogenous nucleic acid material can include the nucleic acid encoding the siRNA together with a promoter to control transcription. The promoter characteristically has a specific nucleotide sequence necessary to initiate transcription. The exogenous nucleic acid material may further include additional sequences (i.e., enhancers) required to obtain the desired gene transcription activity. For the purpose of this discussion an "enhancer" is simply any non-translated DNA sequence that works with the coding sequence (in cis) to change the basal transcription level dictated by the promoter. The exogenous nucleic acid material may be introduced into the cell genome immediately downstream from the promoter so that the promoter and coding sequence are operatively linked so as to permit transcription of the coding sequence. An expression vector can include an exogenous promoter element to control transcription of the inserted exogenous gene. Such exogenous promoters include both constitutive and regulatable promoters.

Naturally-occurring constitutive promoters control the expression of essential cell functions. As a result, a nucleic acid sequence under the control of a constitutive promoter is expressed under all conditions of cell growth. Constitutive promoters include the promoters for the following genes which encode certain constitutive or "housekeeping" functions: hypoxanthine phosphoribosyl transferase (HPRT), dihydrofolate reductase (DHFR), adenosine deaminase, phosphoglycerol kinase (PGK), pyruvate kinase, phosphoglycerol mutase, the beta☐-actin promoter, and other constitutive promoters known to those of skill in the art. In addition, many viral promoters function constitutively in eukaryotic cells. These include: the early and late promoters of SV40; the long terminal repeats (LTRs) of Moloney Leukemia Virus and other retroviruses; and the thymidine kinase promoter of Herpes Simplex Virus, among many others.

Nucleic acid sequences that are under the control of regulatable promoters are expressed only or to a greater or lesser degree in the presence of an inducing or repressing agent, (e.g., transcription under control of the metallothionein promoter is greatly increased in presence of certain metal ions). Regulatable promoters include responsive elements (REs) that stimulate transcription when their inducing factors are bound. For example, there are REs for serum factors, steroid hormones, retinoic acid, cyclic AMP, and tetracycline and doxycycline. Promoters containing a particular RE can be chosen in order to obtain an regulatable response and in some cases, the RE itself may be attached to a different promoter, thereby conferring regulatability to the encoded nucleic acid sequence. Thus, by selecting the appropriate promoter (constitutive versus regulatable; strong versus weak), it is possible to control both the existence and level of expression of a nucleic acid sequence in the genetically modified cell. If the nucleic acid sequence is under the control of an regulatable promoter, delivery of the therapeutic agent in situ is triggered by exposing the genetically modified cell in situ to conditions for permitting transcription of the nucleic acid sequence, e.g., by intraperitoneal injection of specific inducers of the regulatable promoters which control transcription of the agent. For example, in situ expression of a nucleic acid sequence under the control of the metallothionein promoter in genetically modified cells is enhanced by contacting the genetically modified cells with a solution containing the appropriate (i.e., inducing) metal ions in situ.

Accordingly, the amount of siRNA generated in situ is regulated by controlling such factors as the nature of the promoter used to direct transcription of the nucleic acid sequence, (i.e., whether the promoter is constitutive or regulatable, strong or weak) and the number of copies of the exogenous nucleic acid sequence encoding a siRNA sequence that are in the cell.

In one embodiment of the present invention, an expression cassette may contain a pol II promoter that is operably linked to a nucleic acid sequence encoding a siRNA. Thus, the pol II promoter, i.e., a RNA polymerase II dependent promoter, initiates the transcription of the siRNA. In another embodiment, the pol II promoter is regulatable.

A pol II promoter may be used in its entirety, or a portion or fragment of the promoter sequence may be used in which the portion maintains the promoter activity. As discussed herein, pol II promoters are known to a skilled person in the art and include the promoter of any protein-encoding gene, e.g., an endogenously regulated gene or a constitutively expressed gene. For example, the promoters of genes regulated by cellular physiological events, e.g., heat shock, oxygen levels and/or carbon monoxide levels, e.g., in hypoxia, may be used in the expression cassettes of the invention. In addition, the promoter of any gene regulated by the presence of a pharmacological agent, e.g., tetracycline and derivatives thereof, as well as heavy metal ions and hormones may be employed in the expression cassettes of the invention. In an embodiment of the invention, the pol II promoter can be the CMV promoter or the RSV promoter. In another embodiment, the pol II promoter is the CMV promoter.

As discussed above, a pol II promoter of the invention may be one naturally associated with an endogenously regulated gene or sequence, as may be obtained by isolating the 5' non-coding sequences located upstream of the coding segment and/or exon. The pol II promoter of the expression cassette can be, for example, the same pol II promoter driving expression of the targeted gene of interest. Alternatively, the nucleic acid sequence encoding the RNAi molecule may be placed under the control of a recombinant or heterologous pol II promoter, which refers to a promoter that is not normally associated with the targeted gene's natural environment. Such promoters include promoters isolated from any eukaryotic cell, and promoters not "naturally occurring," i.e., containing different elements of different transcriptional regulatory regions, and/or mutations that alter expression. In addition to producing nucleic acid sequences of promoters synthetically, sequences may be produced using recombinant cloning and/or nucleic acid amplification technology, including PCR, in connection with the compositions disclosed herein.

In one embodiment, a pol II promoter that effectively directs the expression of the siRNA in the cell type, organelle, and organism chosen for expression will be employed. Those of ordinary skill in the art of molecular biology generally know the use of promoters for protein expression. The promoters employed may be constitutive, tissue-specific, inducible, and/or useful under the appropriate conditions to direct high level expression of the introduced DNA segment, such as is advantageous in the large-scale production of recombinant proteins and/or peptides. The identity of tissue-specific promoters, as well as assays to characterize their activity, is well known to those of ordinary skill in the art.

In addition to at least one promoter and at least one heterologous nucleic acid sequence encoding the siRNA, the expression vector may include a selection gene, for example, a neomycin resistance gene, for facilitating selection of cells that have been transfected or transduced with the expression vector.

Cells can also be transfected with two or more expression vectors, at least one vector containing the nucleic acid sequence(s) encoding the siRNA(s), the other vector containing a selection gene. The selection of a suitable promoter, enhancer, selection gene and/or signal sequence is deemed to be within the scope of one of ordinary skill in the art without undue experimentation.

The following discussion is directed to various utilities of the instant invention. For example, the instant invention has utility as an expression system suitable for silencing the expression of gene(s) of interest.

The instant invention also provides methods for genetically modifying cells of a mammalian recipient in vivo. According to one embodiment, the method comprises introducing an expression vector for expressing a siRNA sequence in cells of the mammalian recipient in situ by, for example, injecting the vector into the recipient.

VI. Delivery Vehicles for the Expression Cassettes of the Invention

Delivery of compounds into tissues and across the blood-brain barrier can be limited by the size and biochemical properties of the compounds. Currently, efficient delivery of compounds into cells in vivo can be achieved only when the molecules are small (usually less than 600 Daltons). Gene transfer for the correction of inborn errors of metabolism and neurodegenerative diseases of the central nervous system (CNS), and for the treatment of cancer has been accomplished with recombinant adenoviral vectors.

The selection and optimization of a particular expression vector for expressing a specific siRNA in a cell can be accomplished by obtaining the nucleic acid sequence of the siRNA, possibly with one or more appropriate control regions (e.g., promoter, insertion sequence); preparing a vector construct comprising the vector into which is inserted the nucleic acid sequence encoding the siRNA; transfecting or transducing cultured cells in vitro with the vector construct; and determining whether the siRNA is present in the cultured cells.

Vectors for cell gene therapy include viruses, such as replication-deficient viruses (described in detail below). Exemplary viral vectors are derived from Harvey Sarcoma virus, ROUS Sarcoma virus, (MPSV), Moloney murine leukemia virus and DNA viruses (e.g., adenovirus).

Replication-deficient retroviruses are capable of directing synthesis of all virion proteins, but are incapable of making infectious particles. Accordingly, these genetically altered retroviral expression vectors have general utility for high-efficiency transduction of nucleic acid sequences in cultured cells, and specific utility for use in the method of the present invention. Such retroviruses further have utility for the efficient transduction of nucleic acid sequences into cells in vivo. Retroviruses have been used extensively for transferring nucleic acid material into cells. Protocols for producing replication-deficient retroviruses (including the steps of incorporation of exogenous nucleic acid material into a plasmid, transfection of a packaging cell line with plasmid, production of recombinant retroviruses by the packaging cell line, collection of viral particles from tissue culture media, and infection of the target cells with the viral particles) are well known in the art.

An advantage of using retroviruses for gene therapy is that the viruses insert the nucleic acid sequence encoding the siRNA into the host cell genome, thereby permitting the nucleic acid sequence encoding the siRNA to be passed on to the progeny of the cell when it divides. Promoter sequences in the LTR region have can enhance expression of an inserted coding sequence in a variety of cell types. Some disadvantages of using a retrovirus expression vector are (1) insertional mutagenesis, i.e., the insertion of the nucleic acid sequence encoding the siRNA into an undesirable position in the target cell genome which, for example, leads to unregulated cell growth and (2) the need for target cell proliferation in order for the nucleic acid sequence encoding the siRNA carried by the vector to be integrated into the target genome.

Another viral candidate useful as an expression vector for transformation of cells is the adenovirus, a double-stranded DNA virus. The adenovirus is infective in a wide range of cell types, including, for example, muscle and endothelial cells.

Adenoviruses (Ad) are double-stranded linear DNA viruses with a 36 kb genome. Several features of adenovirus have made them useful as transgene delivery vehicles for therapeutic applications, such as facilitating in vivo gene delivery. Recombinant adenovirus vectors have been shown to be capable of efficient in situ gene transfer to parenchymal cells of various organs, including the lung, brain, pancreas, gallbladder, and liver. This has allowed the use of these vectors in methods for treating inherited genetic diseases, such as cystic fibrosis, where vectors may be delivered to a target organ. In addition, the ability of the adenovirus vector to accomplish in situ tumor transduction has allowed the development of a variety of anticancer gene therapy methods for non-disseminated disease. In these methods, vector containment favors tumor cell-specific transduction.

Like the retrovirus, the adenovirus genome is adaptable for use as an expression vector for gene therapy, i.e., by removing the genetic information that controls production of the virus itself. Because the adenovirus functions in an extrachromosomal fashion, the recombinant adenovirus does not have the theoretical problem of insertional mutagenesis.

Several approaches traditionally have been used to generate the recombinant adenoviruses. One approach involves direct ligation of restriction endonuclease fragments containing a nucleic acid sequence of interest to portions of the adenoviral genome. Alternatively, the nucleic acid sequence of interest may be inserted into a defective adenovirus by homologous recombination results. The desired recombinants are identified by screening individual plaques generated in a lawn of complementation cells.

Most adenovirus vectors are based on the adenovirus type 5 (Ad5) backbone in which an expression cassette containing the nucleic acid sequence of interest has been introduced in place of the early region 1 (E1) or early region 3 (E3). Viruses in which E1 has been deleted are defective for replication and are propagated in human complementation cells (e.g., 293 or 911 cells), which supply the missing gene E1 and pIX in trans.

In one embodiment of the present invention, one will desire to generate an RNAi molecule in a brain cell or brain tissue. A suitable vector for this application is an FIV vector or an AAV vector. For example, one may use AAV5. Also, one may apply poliovirus or HSV vectors.

Application of siRNA is generally accomplished by transfection of synthetic siRNAs, in vitro synthesized RNAs, or plasmids expressing short hairpin RNAs (shRNAs). More recently, viruses have been employed for in vitro studies and to generate transgenic mouse knock-downs of targeted genes. Recombinant adenovirus, adeno-associated virus (AAV) and feline immunodeficiency virus (FIV) can be used to deliver genes in vitro and in vivo. Each has its own advantages and disadvantages. Adenoviruses are double stranded DNA viruses with large genomes (36 kb) and have been engineered to accommodate expression cassettes in distinct regions. The inventors previously have used recombinant adenoviruses expressing siRNAs to demonstrate successful viral-mediated gene suppression in brain.

Adeno-associated viruses have encapsidated genomes, similar to Ad, but are smaller in size and packaging capacity (~30 nm vs. ~100 nm; packaging limit of ~4.5 kb). AAV contain single stranded DNA genomes of the + or the − strand. Eight serotypes of AAV (1-8) have been studied extensively, three of which have been evaluated in the brain. An important consideration for the present application is that AAV5 transduces striatal and cortical neurons, and is not associated with any known pathologies.

Adeno associated virus (AAV) is a small nonpathogenic virus of the parvoviridae family. AAV is distinct from the other members of this family by its dependence upon a helper virus for replication. In the absence of a helper virus, AAV may integrate in a locus specific manner into the q arm of chromosome 19. The approximately 5 kb genome of AAV consists of one segment of single stranded DNA of either plus or minus polarity. The ends of the genome are short inverted terminal repeats which can fold into hairpin structures and serve as the origin of viral DNA replication. Physically, the parvovirus virion is non-enveloped and its icosohedral capsid is approximately 20 nm in diameter.

To-date seven serologically distinct AAVs have been identified and five have been isolated from humans or primates and are referred to as AAV types 1-5. The most extensively studied of these isolates is AAV type 2 (AAV2). The genome of AAV2 is 4680 nucleotides in length and contains two open reading frames (ORFs). The left ORF encodes the non-structural Rep proteins, Rep40, Rep 52, Rep68 and Rep 78, which are involved in regulation of replication and transcription in addition to the production of single-stranded progeny genomes. Furthermore, two of the Rep proteins have been associated with the possible integration of AAV genomes into a region of the q-arm of human chromosome 19. Rep68/78 has also been shown to possess NTP binding activity as well as DNA and RNA helicase activities. The Rep proteins possess a nuclear localization signal as well as several potential phosphorylation sites. Mutation of one of these kinase sites resulted in a loss of replication activity.

The ends of the genome are short inverted terminal repeats which have the potential to fold into T-shaped hairpin structures that serve as the origin of viral DNA replication. Within the ITR region two elements have been described which are central to the function of the ITR, a GAGC repeat motif and the terminal resolution site (trs). The repeat motif has been shown to bind Rep when the ITR is in either a linear or hairpin conformation. This binding serves to position Rep68/78 for cleavage at the trs which occurs in a site- and strand-specific manner. In addition to their role in replication, these two elements appear to be central to viral integration. Contained within the chromosome 19 integration locus is a Rep binding site with an adjacent trs. These elements have been shown to be functional and necessary for locus specific integration.

The AAV2 virion is a non-enveloped, icosahedral particle approximately 25 nm in diameter, consisting of three related proteins referred to as VP1,2 and 3. The right ORF encodes the capsid proteins, VP1, VP2, and VP3. These proteins are found in a ratio of 1:1:10 respectively and are all derived from the right-hand ORF. The capsid proteins differ from each other by the use of alternative splicing and an unusual start codon. Deletion analysis has shown that removal or alteration of VP1 which is translated from an alternatively spliced message results in a reduced yield of infections particles. Mutations within the VP3 coding region result in the failure to produce any single-stranded progeny DNA or infectious particles.

The following features of AAV have made it an attractive vector for gene transfer. AAV vectors have been shown in vitro to stably integrate into the cellular genome; possess a broad host range; transduce both dividing and non dividing cells in vitro and in vivo and maintain high levels of expression of the transduced genes. Viral particles are heat stable, resistant to solvents, detergents, changes in pH, temperature, and can be concentrated on CsCl gradients. Integration of AAV provirus is not associated with any long term negative effects on cell growth or differentiation. The ITRs have been shown to be the only cis elements required for replication, packaging and integration and may contain some promoter activities.

Further provided by this invention are chimeric viruses where AAV can be combined with herpes virus, herpes virus amplicons, baculovirus or other viruses to achieve a desired tropism associated with another virus. For example, the AAV4 ITRs could be inserted in the herpes virus and cells could be infected. Post-infection, the ITRs of AAV4 could be acted on by AAV4 rep provided in the system or in a separate vehicle to rescue AAV4 from the genome. Therefore, the cellular tropism of the herpes simplex virus can be combined with AAV4 rep mediated targeted integration. Other viruses that could be utilized to construct chimeric viruses include lentivirus, retrovirus, pseudotyped retroviral vectors, and adenoviral vectors.

Also provided by this invention are variant AAV vectors. For example, the sequence of a native AAV, such as AAV5, can be modified at individual nucleotides. The present invention includes native and mutant AAV vectors. The present invention further includes all AAV serotypes.

FIV is an enveloped virus with a strong safety profile in humans; individuals bitten or scratched by FIV-infected cats do not seroconvert and have not been reported to show any signs of disease. Like AAV, FIV provides lasting transgene expression in mouse and nonhuman primate neurons, and transduction can be directed to different cell types by pseudotyping, the process of exchanging the virus' native envelope for an envelope from another virus.

Thus, as will be apparent to one of ordinary skill in the art, a variety of suitable viral expression vectors are available for transferring exogenous nucleic acid material into cells. The selection of an appropriate expression vector to express a therapeutic agent for a particular condition amenable to gene silencing therapy and the optimization of the conditions for insertion of the selected expression vector into the cell, are within the scope of one of ordinary skill in the art without the need for undue experimentation.

In another embodiment, the expression vector is in the form of a plasmid, which is transferred into the target cells by one of a variety of methods: physical (e.g., microinjection, electroporation, scrape loading, microparticle bombardment) or by cellular uptake as a chemical complex (e.g., calcium or strontium co-precipitation, complexation with lipid, complexation with ligand). Several commercial products are available for cationic liposome complexation including Lipofectin™ (Gibco-BRL, Gaithersburg, Md.) and Transfectam™ (ProMega, Madison, Wis.). However, the efficiency of transfection by these methods is highly dependent on the nature of the target cell and accordingly, the conditions for optimal transfection of nucleic acids into cells using the above-mentioned procedures must be optimized. Such optimization is within the scope of one of ordinary skill in the art without the need for undue experimentation.

VII. Diseases and Conditions Amendable to the Methods of the Invention

In the certain embodiments of the present invention, a mammalian recipient to an expression cassette of the invention has a condition that is amenable to gene silencing therapy. As used herein, "gene silencing therapy" refers to administration to the recipient exogenous nucleic acid material encoding a therapeutic siRNA and subsequent expression of the administered nucleic acid material in situ. Thus, the phrase "condition amenable to siRNA therapy" embraces conditions such as genetic diseases (i.e., a disease condition that is attributable to one or more gene defects), acquired pathologies (i.e., a pathological condition that is not attributable to an inborn defect), cancers, neurodegenerative diseases, e.g., trinucleotide repeat disorders, and prophylactic processes (i.e., prevention of a disease or of an undesired medical condition). A gene "associated with a condition" is a gene that is either the cause, or is part of the cause, of the condition to be treated. Examples of such genes include genes associated with a neurodegenerative disease (e.g., a trinucleotide-repeat disease such as a disease associated with polyglutamine repeats, Huntington's disease, and several spinocerebellar ataxias), and genes encoding ligands for chemokines involved in the migration of a cancer cells, or chemokine receptor. Also siRNA expressed from viral vectors may be used for in vivo antiviral therapy using the vector systems described.

Accordingly, as used herein, the term "therapeutic siRNA" refers to any siRNA that has a beneficial effect on the recipient. Thus, "therapeutic siRNA" embraces both therapeutic and prophylactic siRNA.

Differences between alleles that are amenable to targeting by siRNA include disease-causing mutations as well as polymorphisms that are not themselves mutations, but may be linked to a mutation or associated with a predisposition to a disease state. An example of a targetable polymorphism that is not itself a mutation is the polymorphism in exon 58 associated with Huntington's disease.

Single nucleotide polymorphisms comprise most of the genetic diversity between humans. The major risk factor for developing Alzheimer's disease is the presence of a particular polymorphism in the apolipoprotein E gene.

Single nucleotide polymorphisms comprise most of the genetic diversity between humans, and that many disease genes, including the HD gene in Huntington's disease, contain numerous single nucleotide or multiple nucleotide polymorphisms that could be separately targeted in one allele vs. the other. The major risk factor for developing Alzheimer's disease is the presence of a particular polymorphism in the apolipoprotein E gene.

A. Gene Defects

A number of diseases caused by gene defects have been identified. For example, this strategy can be applied to a major class of disabling neurological disorders. For example this strategy can be applied to the polyglutamine diseases, as is demonstrated by the reduction of polyglutamine aggregation in cells following application of the strategy. The neurodegenerative disease may be a trinucleotide-repeat disease, such as a disease associated with polyglutamine repeats, including Huntington's disease, and several spinocerebellar ataxias. Additionally, this strategy can be applied to a non-degenerative neurological disorder, such as DYT1 dystonia.

B. Acquired Pathologies

As used herein, "acquired pathology" refers to a disease or syndrome manifested by an abnormal physiological, biochemical, cellular, structural, or molecular biological state. For example, the disease could be a viral disease, such as hepatitis or AIDS.

C. Cancers

The condition amenable to gene silencing therapy alternatively can be a genetic disorder or an acquired pathology that is manifested by abnormal cell proliferation, e.g., cancer. According to this embodiment, the instant invention is useful for silencing a gene involved in neoplastic activity. The present invention can also be used to inhibit overexpression of one or several genes. The present invention can be used to treat neuroblastoma, medulloblastoma, or glioblastoma.

IX. Dosages, Formulations and Routes of Administration of the Agents of the Invention The agents of the invention are preferably administered so as to result in a reduction in at least one symptom associated with a disease. The amount administered will vary depending on various factors including, but not limited to, the composition chosen, the particular disease, the weight, the physical condition, and the age of the mammal, and whether prevention or treatment is to be achieved. Such factors can be readily determined by the clinician employing animal models or other test systems, which are well known to the art.

Administration of siRNA may be accomplished through the administration of the nucleic acid molecule encoding the RNAi molecule. Pharmaceutical formulations, dosages and routes of administration for nucleic acids are generally known in the art.

The present invention envisions treating a disease, for example, a neurodegenerative disease, in a mammal by the administration of an agent, e.g., a nucleic acid composition, an expression vector, or a viral particle of the invention. Administration of the therapeutic agents in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. Both local and systemic administration is contemplated.

One or more suitable unit dosage forms having the therapeutic agent(s) of the invention, which, as discussed below, may optionally be formulated for sustained release (for example using microencapsulation), can be administered by a variety of routes including parenteral, including by intravenous and intramuscular routes, as well as by direct injection into the diseased tissue. For example, the therapeutic agent may be directly injected into the brain. Alternatively the therapeutic agent may be introduced intrathecally for brain and spinal cord conditions. In another example, the therapeutic agent may be introduced intramuscularly for viruses that traffic back to affected neurons from muscle, such as AAV, lentivirus and adenovirus. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for administration, they are preferably combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" is a carrier, diluent, excipient, and/or salt that is compatible with the other ingredients of the formulation, and not deleterious to the recipient thereof. The active ingredient for administration may be present as a powder or as granules, as a solution, a suspension or an emulsion.

Pharmaceutical formulations containing the therapeutic agents of the invention can be prepared by procedures known in the art using well known and readily available ingredients. The therapeutic agents of the invention can also be formulated as solutions appropriate for parenteral administration, for instance by intramuscular, subcutaneous or intravenous routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

It will be appreciated that the unit content of active ingredient or ingredients contained in an individual aerosol dose of each dosage form need not in itself constitute an effective amount for treating the particular indication or disease since the necessary effective amount can be reached by administration of a plurality of dosage units. Moreover, the effective amount may be achieved using less than the dose in the dosage form, either individually, or in a series of administrations.

The pharmaceutical formulations of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions such as phosphate buffered saline solutions pH 7.0-8.0. saline solutions and water.

The invention will now be illustrated by the following non-limiting Examples.

Example 1

RNAi-Mediated Silencing of Genes

The inventors have previously shown that genes can be silenced in an allele-specific manner. They have also demonstrated that viral-mediated delivery of siRNA can specifically reduce expression of targeted genes in various cell types, both in vitro and in vivo. This strategy was then applied to reduce expression of a neurotoxic polyglutamine disease protein. The ability of viral vectors to transduce cells efficiently in vivo, coupled with the efficacy of virally expressed siRNA shown here, extends the application of siRNA to viral-based therapies and in vivo targeting experiments that aim to define the function of specific genes.

Huntington's disease (HD) is one of several dominant neurodegenerative diseases that result from a similar toxic gain of function mutation in the disease protein: expansion of a polyglutamine (polyQ)-encoding tract. It is well established that for HD and other polyglutamine diseases, the length of the expansion correlates inversely with age of disease onset. Animal models for HD have provided important clues as to how mutant huntingtin (htt) induces pathogenesis. Currently, no neuroprotective treatment exists for HD. RNA interference has emerged as a leading candidate approach to reduce expression of disease genes by targeting the encoding mRNA for degradation.

Although the effect of partial reduction of wildtype htt in adult neurons is unknown, it is advantageous to target only mutant htt for degradation, if possible. Disease allele-specific RNAi are designed using approaches that led to allele specific silencing for other neurogenetic disease models. This allows directed silencing of the mutant, disease-causing expanded allele, leaving the normal allele intact.

Constitutive expression of shRNA can prevent the neuropathological and behavioral phenotypes in a mouse model of Spinocerebellar Ataxia type I, a related polyQ disease. However, the constitutive expression of shRNA may not be necessary, particularly for pathologies that take many years to develop but may be cleared in a few weeks or months. For this reason, and to reduce long-term effects that may arise if nonspecific silencing or activation of interferon responses is noted, controlled expression may be very important. In order to regulate RNAi for disease application, doxycycline-responsive vectors have been developed for controlled silencing in vitro.

Most eukaryotes encode a substantial number of small noncoding RNAs termed micro RNAs (miRNAs). mir-30 is a 22-nucleotide human miRNA that can be naturally processed from a longer transcript bearing the proposed miR-30 stem-loop precursor. mir-30 can translationally inhibit an mRNA-bearing artificial target sites. The mir-30 precursor stem can be substituted with a heterologous stem, which can be processed to yield novel miRNAs and can block the expression of endogenous mRNAs.

Two strategies are possible to target a particular sequence, such as the gene involved in Huntington's Disease (FIGS. 1A and 1B). One can develop non-allele specific RNAi molecules, and candidates based on 8.2 inhibitory RNAs have been developed. Alternatively, one can develop allele-specific RNAi molecules. The inventors have worked to develop RNAi molecules that target several key single nucleotide polymorphisms (SNPs). These RNAi molecules, however, may be limited to the treatment of specific families/patients.

Another approach, which is the approach used in the present invention, the inventors targeted the expansion region. This approach has the advantage of being able to treat entire HD populations, and not just those with specific SNPs. These RNAi molecules are different because instead of targeting a SNP for allele specificity, these sequences take advantage of structural integrity at the sites flanking the expansion region. The siRNA data shows that they are effective. The present inventors have also moved them into miRNA expression vectors, which were also effective.

The inventors have generated and tested the following RNAi molecules:

| siRNA | Sequence |
|---|---|
| HDAS 07 | AUGAAGGCCUUCGAGUCCCUC (SEQ ID NO: 1) |
| HDAS 18 | GGCGACCCUGGAAAAGCUGAU (SEQ ID NO: 2) |
| HDAS 19 | UGGCGACCCUGGAAAAGCUGA (SEQ ID NO: 3) |
| HDAS 20 | AUGGCGACCCUGGAAAAGCUG (SEQ ID NO: 4) |

Sequence miHD7A1
(SEQ ID NO: 5)
AAAACUCGAGUGAGCGCUGAAGGCCUUCGAGUCCCUCA*CCGUAAAGC CACAGAUGGG*UGAGGGACUCGAAGGCCUUCAUCGCCUACUAGUAAAA Sequence miHD7A2
(SEQ ID NO: 6)
AAAACUCGAGUGAGCGCUGAAGGCCUUCGAGUCUUUUA*CCGUAAAGC CACAGAUGGG*UGAGGGACUCGAAGGCCUUCAUCGCCUACUAGUAAAA Sequence miHD7B1
(SEQ ID NO: 7)
AAAACUCGAGUGAGCGCAUGAAGGCCUUCGAGUCCCUC*CCGUAAAGC CACAGAUGGG*GAGGGACUCGAAGGCCUUCAUCCGCCUACUAGUAAAA Sequence miHD7B2
(SEQ ID NO: 8)
AAAACUCGAGUGAGCGCAUGAAGGCCUUCGAGUCUUUU*CCGUAAAGC CACAGAUGGG*GAGGGACUCGAAGGCCUUCAUCCGCCUACUAGUAAAA The different fonts show the various parts of the miRNA. In sequential order, the stem sequence of the miRNA is shown in bold, then the sense strand in regular type, then the loop sequence in bold italics, then the anti-sense strand in regular type, and last, part of stem sequence in bold.

The inventors generated constructs to assess allele-specific silencing of Htt (FIGS. 2A and 2B). Two plasmids were generated expressing full-length wild type (FIG. 2A, pCMV-FLHtt 18Q-Flag) or mutant huntingtin (FIG. 2B, pCMV-FLHtt 83Q-V5). Wild type and mutant full-length huntingtin are expressed under the control of the CMV promoter and each cDNA have distinct epitope tags to differentiate its expression by western blot. To normalize transfection efficiencies either renilla (WT htt) or firefly (mutant htt) luciferase were included on the same plasmid. This design allowed assessment of allele specificity in the same cell after co-transfection.

Figure 3A:
Figure 3B:
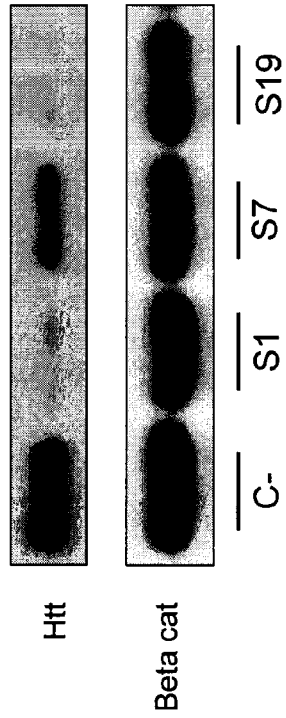

Western blot and Q-PCR results indicate that the candidate siRNAs were allele-specific in targeting mutant Htt, but not wild type Htt (FIGS. 3A-3C). HEK293 cells were co-transfected with plasmids expressing wild type and mutant huntingtin and with different siRNA sequence. Total RNA and protein lysates were obtained 24 hours after transfection. After screening by Q-PCR and western blot, some of the siRNA design sequences were observed to preferentially silence the mutant allele. FIG. 3A shows wild type Htt and FIG. 3B shows mutant Htt. As seen in FIG. 3C, siRNA sequence number 7 (S7) reduced mutant htt by 40% and the wild type huntingtin by 6%.

The inventors found that formulated LNP siRNAs were distributed broadly following intrastriatal infusion, that formulated LNP siRNA reduced Htt in adult mouse brain at biologically relevant dose, and siRNAs targeting sequences targeting the expansion provided for allele specific silencing.

Figure 4:
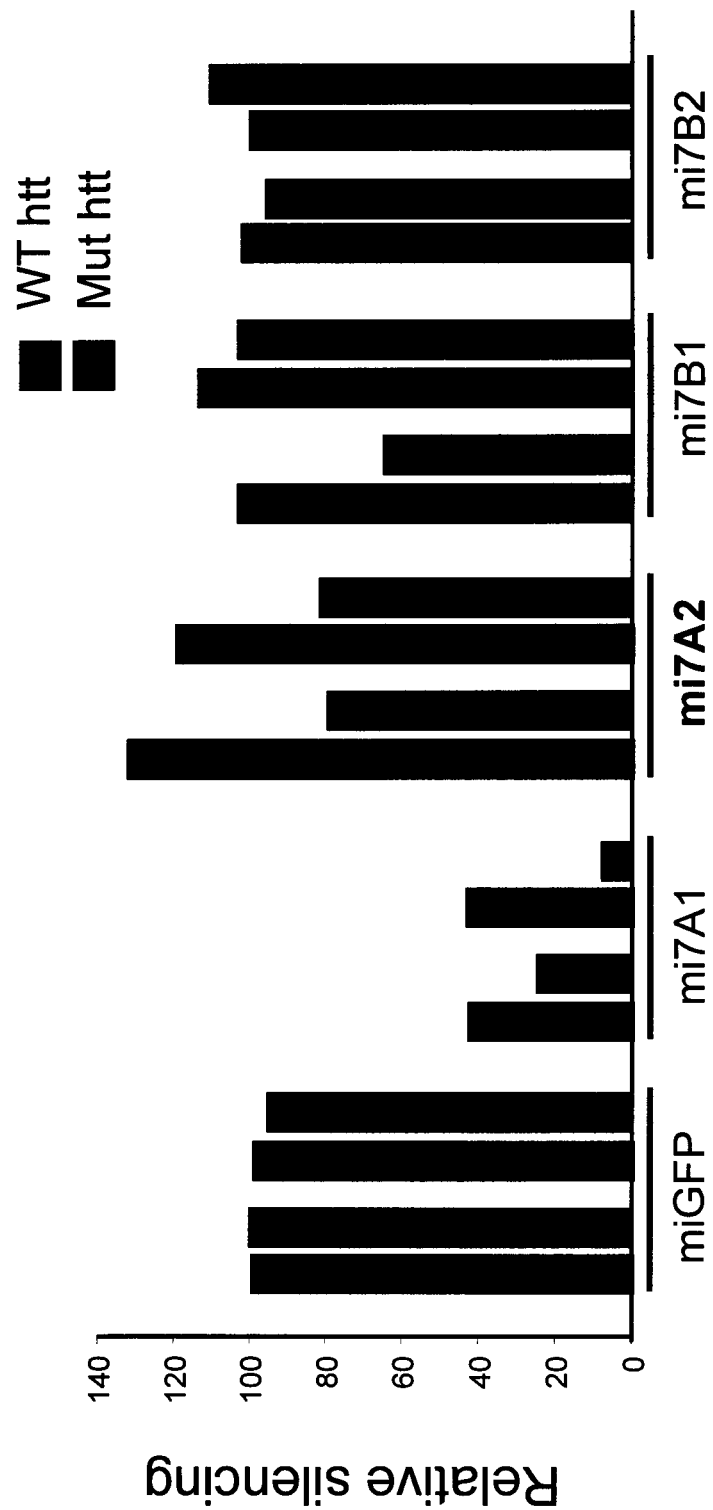
FIG. 4 shows the results of miRNA shuttles for allele-specific silencing of htt. Data represents the densitometry analysis of wild type and mutant Htt expression for different protein lysates.

The inventors also found that miRNA shuttles for allele specific silencing of htt could effectively be used (FIG. 4). miRNA shuttles based on the siRNA sequence 7 (S7) were generated. To assess silence specificity, HEK293 cells were co-transfected with wild type and mutant huntingtin plasmids and mi7A1, mi7A2, mi7B1, mi7B2 or miGFP as a control. Cells were harvested 24 hours after transfection and wild type and mutant Htt silencing was determined by western blot. Mi7A1 and mi7A2 had the most preferential silencing profile, the latter the most beneficial.

Figure 5:
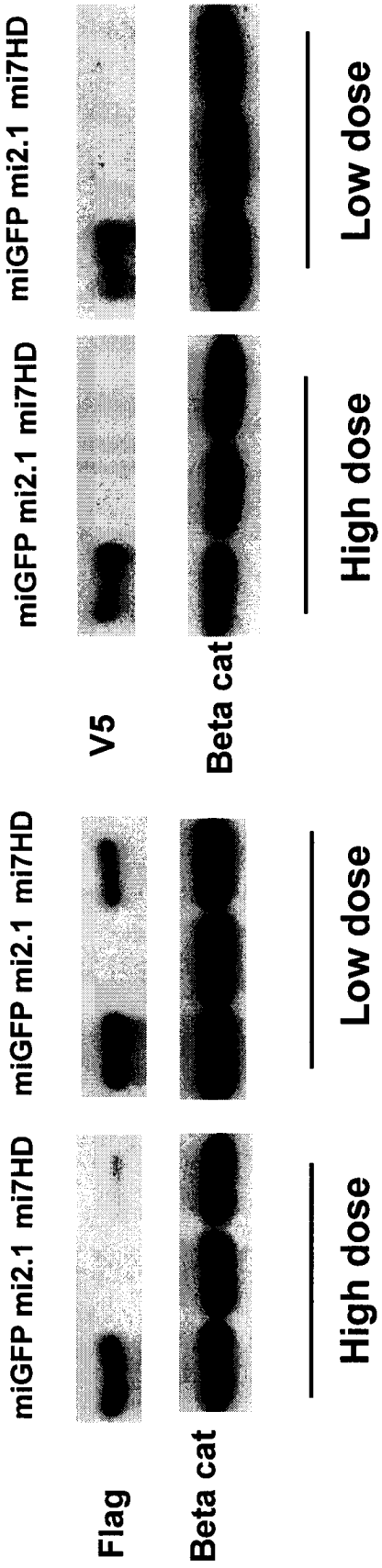
FIGS. 5A and 5B. Dose response of mi7A1 sequence.

Sequence mi7A1 silences very efficiently either wild type or mutant huntingtin. This is possibly due to an excess of mi7A1 production. The specificity of silencing of mi7A1 at high and low doses was compared. HEK293 cells were transfected with two different amounts of mi7A1 and protein lysates were obtained 24 hours after transfection. Silencing of both wild type and mutant huntingtin was determined by western blot with specific antibodies against the epitope tags (FIGS. 5A and 5B). Data shows that preferential silencing for the mutant huntingtin is achieved when mi7A1 is transfected at a low dose. FIG. 5A shows normal Htt, and FIG. 5B shows mutant Htt.

Figure 6:
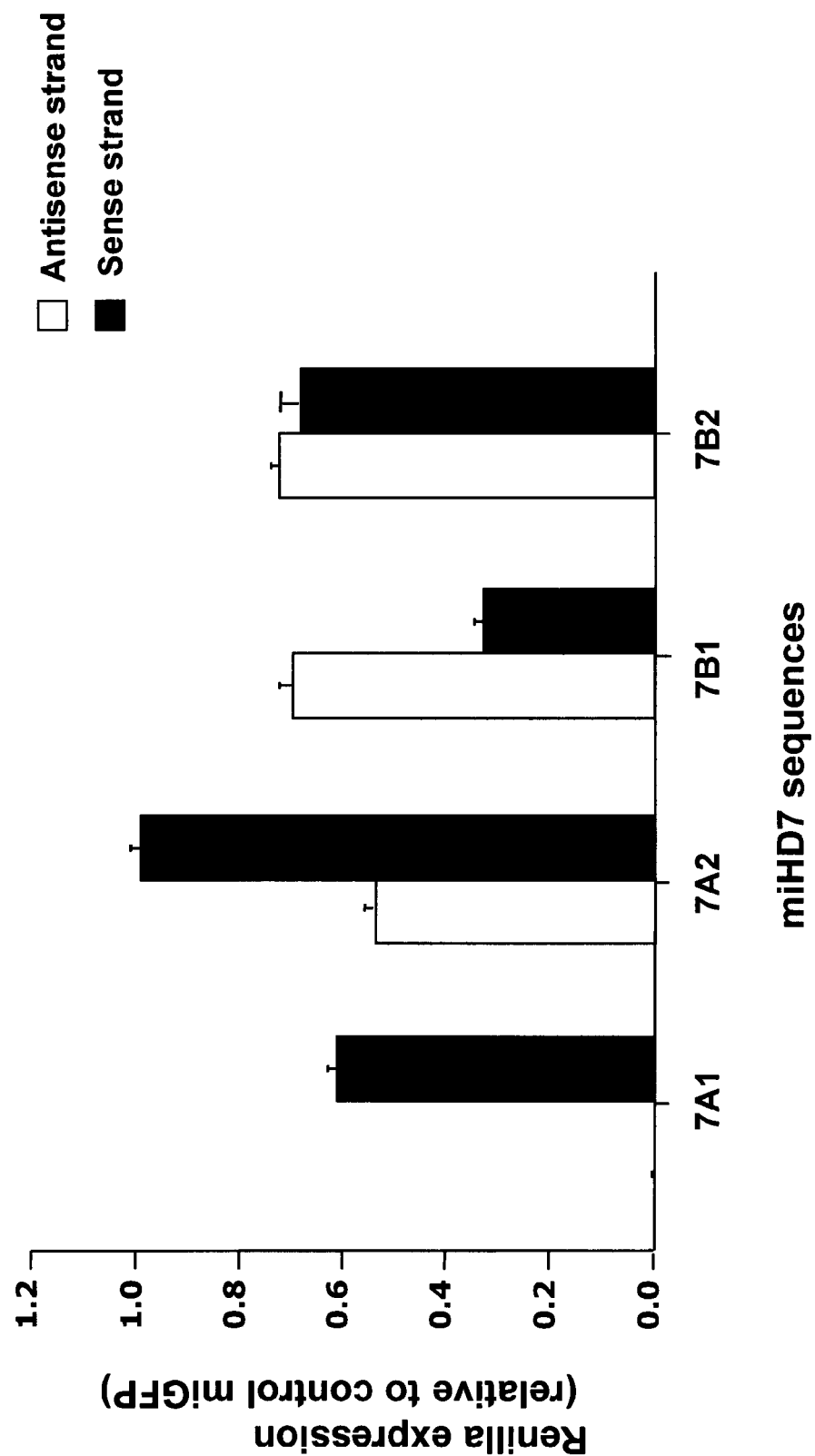
FIG. 6. Strand biasing of miR shuttles. Data represents relative luciferase expression of the reporter constructs for each specific strand after mil shuttle transfection. All data is compared to cells transfected with each reporter constructs and a miRNA control (miGFP).

The inventors also evaluated the strand biasing of miR shuttles (FIG. 6). Different mutations were introduced to the 3' end of the sense strand of the mi7 sequences (mi7A2 and mi7B2) to promote antisense strand loading into the RISC. To determine which strand was preferentially loaded several luciferase reporter constructs based on psicheck2 vector were designed. HEK293 cells were cotransfected with both mi7 shuttle and a reporter construct for each strand and 24 hours later cell extracts were obtained. Sequences 7A1 and 7A2 showed exceptional strand biasing.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An expression cassette comprising a nucleic acid encoding an miRNA comprising a stem sequence, a sense strand of 15 to 30 nucleotides in length, a loop sequence of 4 to 50 nucleotides in length, an antisense strand 15 to 30 nucleotides in length, and a stem sequence, wherein the miRNA has at least 80% sequence identity compared to full-length miHD7A-2 (SEQ ID NO:6), miHD7B-1 (SEQ ID NO:7), or miHD7B-2 (SEQ ID NO:8).

2. The expression cassette of claim 1, further comprising a promoter.

3. The expression cassette of claim 2, wherein the promoter is a CMV, RSV, pol II or pol III promoter.

4. The expression cassette of claim 1, further comprising a marker gene.

5. A vector comprising the expression cassette of claim 1.

6. The vector of claim 5, wherein the vector is an adenoviral, lentiviral, adeno-associated viral (AAV), poliovirus, HSV, or murine Maloney-based viral vector.

7. A cell comprising:
(a) an expression cassette comprising a nucleic acid having at least 80% sequence identity compared to full-length miHD7A-2 (SEQ ID NO:6), miHD7B-1 (SEQ ID NO:7), or miHD7B-2 (SEQ ID NO:8); or
(b) a vector comprising an expression cassette, wherein the expression cassette comprises a nucleic acid encoding an miRNA comprising a stem sequence, a sense strand of 15 to 30 nucleotides in length, a loop sequence of 4 to 50 nucleotides in length, an antisense strand 15 to 30 nucleotides in length, and a stem sequence, wherein the miRNA has at least 80% sequence identity compared to full-length miHD7A-2 (SEQ ID NO:6), miHD7B-1 (SEQ ID NO:7), or miHD7B-2 (SEQ ID NO:8).

8. An isolated or purified miRNA comprising a stem sequence, a sense strand of 15 to 30 nucleotides in length, a loop sequence of 4 to 50 nucleotides in length, an antisense strand 15 to 30 nucleotides in length, and a stem sequence, wherein the miRNA has at least 80% sequence identity compared to full-length miHD7A-2 (SEQ ID NO:6), miHD7B-1 (SEQ ID NO:7), or miHD7B-2 (SEQ ID NO:8).

9. The vector of claim 5, wherein the vector is an AAV vector.

10. An expression cassette comprising a nucleic acid encoding an miRNA comprising a stem sequence, a sense strand of 15 to 30 nucleotides in length, a loop sequence of 4 to 50 nucleotides in length, an antisense strand 15 to 30 nucleotides in length, and a stem sequence, wherein the miRNA is miHD7A-2 (SEQ ID NO:6), miHD7B-1 (SEQ ID NO:7), or miHD7B-2 (SEQ ID NO:8).

11. An isolated or purified miRNA comprising a stem sequence, a sense strand of 15 to 30 nucleotides in length, a loop sequence of 4 to 50 nucleotides in length, an antisense strand 15 to 30 nucleotides in length, and a stem sequence, wherein the miRNA is miHD7A-2 (SEQ ID NO:6), miHD7B-1 (SEQ ID NO:7), or miHD7B-2 (SEQ ID NO:8).

12. The expression cassette of claim 1, wherein the miRNA has at least 80% sequence identity compared to full-length miHD7A-2 (SEQ ID NO:6).

13. The expression cassette of claim 1, wherein the miRNA has at least 80% sequence identity compared to full-length miHD7B-1 (SEQ ID NO:7).

14. The expression cassette of claim 1, wherein the miRNA has at least 80% sequence identity compared to full-length miHD7B-2 (SEQ ID NO:8).

15. The expression cassette of claim 10, wherein the miRNA is miHD7A-2 (SEQ ID NO:6).

16. The expression cassette of claim 10, wherein the miRNA is miHD7B-1 (SEQ ID NO:7).

17. The expression cassette of claim 10, wherein the miRNA is miHD7B-2 (SEQ ID NO:8).

* * * * *